(12) United States Patent
Koh et al.

(10) Patent No.: US 7,946,995 B1
(45) Date of Patent: May 24, 2011

(54) ANALYZING CIRCADIAN VARIATIONS OF A HEMODYNAMIC PARAMETER TO DETERMINE AN ADVERSE CARDIAC CONDITION

(75) Inventors: Steve Koh, South Pasadena, CA (US); Euljoon Park, Valencia, CA (US); Dorin Panescu, San Jose, CA (US)

(73) Assignee: Pacesetter, Inc., Sylmar, CA (US)

( * ) Notice: Subject to any disclaimer, the term of this patent is extended or adjusted under 35 U.S.C. 154(b) by 534 days.

(21) Appl. No.: 11/558,284

(22) Filed: Nov. 9, 2006

(51) Int. Cl.
*A61B 5/02* (2006.01)

(52) U.S. Cl. ......... 600/485; 600/486; 600/508; 600/513

(58) Field of Classification Search ............... 600/481, 600/483, 485, 486, 500–502, 513, 515–519, 600/504–509; 607/14, 19, 17
See application file for complete search history.

(56) References Cited

U.S. PATENT DOCUMENTS

| | | | |
|---|---|---|---|
| 4,686,988 A | | 8/1987 | Sholder |
| 4,708,142 A | | 11/1987 | DeCote, Jr. |
| 4,729,376 A | | 3/1988 | DeCote, Jr. |
| 4,969,467 A | | 11/1990 | Callaghan et al. |
| 5,350,140 A | | 9/1994 | Kleks et al. |
| 5,466,254 A | | 11/1995 | Helland |
| 5,755,736 A | * | 5/1998 | Gillberg et al. ............ 607/4 |
| 5,865,760 A | * | 2/1999 | Lidman et al. ............ 600/509 |
| 6,058,328 A | * | 5/2000 | Levine et al. ............ 607/14 |
| 6,128,534 A | * | 10/2000 | Park et al. ............ 607/17 |
| 6,328,699 B1 | | 12/2001 | Eigler et al. |
| 6,714,811 B1 | * | 3/2004 | Padmanabhan et al. ...... 600/509 |
| 6,773,404 B2 | | 8/2004 | Poezevera et al. |
| 6,969,369 B2 | | 11/2005 | Struble |
| 6,970,742 B2 | | 11/2005 | Mann et al. |
| 7,115,095 B2 | * | 10/2006 | Eigler et al. ............ 600/486 |
| 7,590,449 B2 | * | 9/2009 | Mann et al. ............ 607/23 |
| 2003/0055345 A1 | | 3/2003 | Eigler et al. |
| 2004/0019285 A1 | | 1/2004 | Eigler et al. |
| 2004/0106874 A1 | | 6/2004 | Eigler et al. |
| 2004/0116819 A1 | * | 6/2004 | Alt ............ 600/513 |
| 2004/0116992 A1 | | 6/2004 | Wardle et al. |
| 2004/0147969 A1 | | 7/2004 | Mann et al. |

(Continued)

FOREIGN PATENT DOCUMENTS

WO  WO01/51123 A1  7/2001

(Continued)

OTHER PUBLICATIONS

Giles, Thomas D., et al.; Circadian Variation in Blood Pressure and Heart Rate in Nonhypertensive Congestive Heart Failure; Journal of Cardiovascular Pharmacology; vol. 28(6) Dec. 1996 pp. 733-740.

(Continued)

*Primary Examiner* — Patricia C Mallari
*Assistant Examiner* — Michael D'Angelo

(57) ABSTRACT

A system and method of determining the status of an adverse cardiac condition of a medical patient based on circadian variation of one or more hemodynamic parameters are provided. In some embodiments, the system and method calculate a first average value of a series of first values during a first time period, a second average value of a series of second values during a second time period, and a difference between the first average value and the second average value. The method provides an indication of an adverse cardiac condition when the difference is less than a predetermined threshold.

12 Claims, 14 Drawing Sheets

U.S. PATENT DOCUMENTS

| | | |
|---|---|---|
| 2005/0136385 A1 | 6/2005 | Mann et al. |
| 2005/0137489 A1* | 6/2005 | Jackson et al. ................. 600/515 |
| 2005/0165456 A1 | 7/2005 | Mann et al. |
| 2005/0177135 A1* | 8/2005 | Hildebrand et al. ....... 604/890.1 |
| 2005/0288596 A1 | 12/2005 | Eigler et al. |
| 2005/0288604 A1 | 12/2005 | Eigler et al. |
| 2005/0288722 A1 | 12/2005 | Eigler et al. |
| 2006/0009810 A1 | 1/2006 | Mann et al. |
| 2006/0079793 A1 | 4/2006 | Mann et al. |
| 2006/0149324 A1 | 7/2006 | Mann et al. |
| 2006/0149327 A1* | 7/2006 | Hedberg et al. ................. 607/23 |
| 2006/0149330 A1 | 7/2006 | Mann et al. |
| 2006/0149331 A1 | 7/2006 | Mann et al. |
| 2008/0114219 A1* | 5/2008 | Zhang et al. ................... 600/301 |

FOREIGN PATENT DOCUMENTS

| | | |
|---|---|---|
| WO | WO2005/062823 A2 | 11/2006 |

OTHER PUBLICATIONS

Guyton, Arthur C.; Effect of Elevated Left Atrial Pressure and Decreased Plasma Protein Concentration on the Development of Pulmonary Edema; Circulation Research, 1959; 7; 649-657.

* cited by examiner

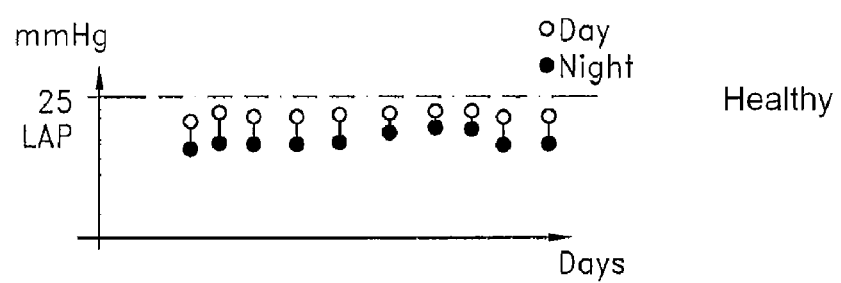
FIG. 5A  Healthy
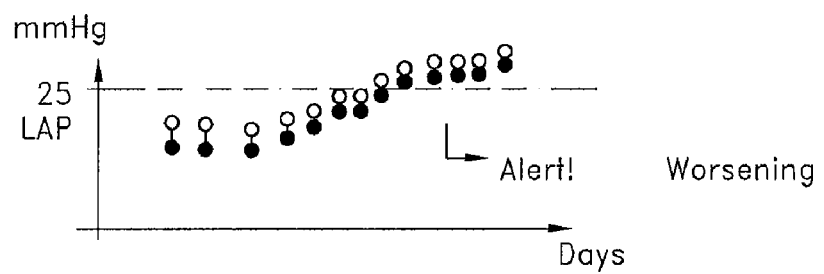
FIG. 5B  Worsening
FIG. 5C  Improving

Figure 5D

| Time | Healthy Individual (mm Hg) | CHF-Prone Individual (mm Hg) |
|---|---|---|
| 12:00 am | 10 | 25 |
| 01:00 am | 10 | 25 |
| 02:00 am | 11 | 24 |
| 03:00 am | 10 | 25 |
| 04:00 am | 11 | 24 |
| 05:00 am | 11 | 24 |
| 06:00 am | 10 | 24 |
| 07:00 am | 12 | 27 |
| 08:00 am | 14 | 26 |
| 09:00 am | 15 | 27 |
| 10:00 am | 15 | 28 |
| 11:00 am | 14 | 27 |
| 12:00 pm | 14 | 28 |
| 01:00 pm | 14 | 28 |
| 02:00 pm | 14 | 28 |
| 03:00 pm | 15 | 27 |
| 04:00 pm | 15 | 28 |
| 05:00 pm | 14 | 27 |
| 06:00 pm | 14 | 28 |
| 07:00 pm | 14 | 28 |
| 08:00 pm | 12 | 26 |
| 09:00 pm | 13 | 26 |
| 10:00 pm | 11 | 24 |
| 11:00 pm | 10 | 25 |

ANALYZING CIRCADIAN VARIATIONS OF A HEMODYNAMIC PARAMETER TO DETERMINE AN ADVERSE CARDIAC CONDITION

BACKGROUND OF THE INVENTION

1. Field of the Invention

The invention relates to the field of implantable medical devices and to systems and methods of monitoring hemodynamic parameters to detect and determine the onset of various medical conditions, such as congestive heart failure and pulmonary edema.

2. Description of the Related Art

A variety of implantable medical devices are known to automatically monitor a patient's physiologic condition and to selectively provide therapy when indicated. Implantable pacemakers and/or cardioverter defibrillators (ICDs) are implantable medical devices configured to monitor a patient's cardiac activity and selectively provide therapy in response to detected cardiac arrhythmias. Cardiac arrhythmia are generally conditions in which the heart muscle contracts irregularly, e.g., faster or slower than normal. Implantable pacemakers and/or ICDs typically include a stimulation pulse generator that generates therapeutic stimulation for delivery to patient tissue. ICDs also typically include and are controlled by a microprocessor-based controller that regulates the delivery of such therapy.

Implantable pacemakers and/or ICDs are also typically configured to monitor the patient's cardiac activity, including a variety of hemodynamic parameters and cardiac signals, in order to detect abnormalities and cardiac arrhythmias. These devices also respond with an appropriate therapy when an abnormality is detected. For example, therapeutic electrical stimulation may be provided when an implantable pacemaker and/or ICD detects a cardiac arrhythmia.

The cardiac signals that are monitored to detect cardiac arrhythmias may also be useful in detecting other potential abnormalities that may be indicative of future heart problems. For example, a consistently low amplitude of the monitored cardiac signal may be indicative of a heart problem which can lead to future heart failure, if not detected early. Thus, the cardiac signals that are monitored can be stored and analyzed for early detection of other potential problems.

Implantable pacemakers, ICDs, and other devices can include sensors to detect any of a variety of hemodynamic parameters. In some cases these devices merely monitor the electrical activity of the heart; however, in many cases, these devices are also configured to detect other parameters, such as the fluid pressure within the heart itself.

Elevated pressure within the left atrium of the heart can indicate the onset of fluid accumulation in the lungs, which often indicates the onset of a condition known as congestive heart failure (CHF). Heart failure is a condition in which a patient's heart works less efficiently than it should due to the heart's failure to sufficiently supply the body with oxygen rich blood. Congestive heart failure is a condition where a person's heart fails to sufficiently supply oxygenated blood to the body accompanied by a build-up of fluid pressure in the pulmonary blood vessels that drain the lungs. Elevated left atrial pressure (LAP) can also lead to a condition known as pulmonary edema, which can cause shortness of breath, hypoxemia, acidosis, respiratory arrest, and death.

Mean left atrial pressure in healthy individuals is normally less than about twelve millimeters of mercury (12 mm Hg). Patients with CHF who have been medically treated and clinically "well compensated" may generally have mean left atrial pressures in the range from 15 to 20 mm Hg. Transudation of fluid into the pulmonary interstitial spaces can generally be expected to occur when the left atrial pressure is about 25 mm Hg. Transudation sometimes occurs at greater pressure levels, for example at more than about 30 mm Hg, in some patients with chronic CHF. Pulmonary edema has been found to be very reliable predicted by reference to left atrial pressures, and much less well correlated with conditions in any other chamber of the heart.

One or more transducers can be implanted at particular locations by an invasive or surgical procedure for the clinical purpose of measuring blood pressure within the body. These locations are well known to those skilled in the art, such as physicians and physiologists, and include the left ventricle, left atrium, pulmonary veins, pulmonary capillaries, the pulmonary arteries, the right ventricle, and the right atrium.

It has been appreciated for many years that, with the exclusion of certain well-known medical conditions, a key left-sided filling parameter determining the state of compensation of the left heart is the mean left atrial pressure (LAP). LAP is closely predicted by the pulmonary venous pressure (PVP), the pulmonary capillary wedge pressure (PCWP), or the pulmonary artery and left ventricular end diastolic pressures (PADP and LVEDP, respectively). Mean RA and end diastolic RV pressures can also be used to predict left sided decompensation. In addition, the RV pressure at the peak of the first derivative of pressure with respect to time during systolic contraction is sometimes used to estimate PADP.

These pressures are complex periodic time varying signals composed of the superposition of cardiac and respiratory component waves. During normal and certain pathologic conditions such as congestive heart failure, these mean or diastolic pressure indices typically vary from 0 to 40 mm Hg gauge pressure referenced to atmospheric pressure. With few exceptions, these pressure indices transiently decrease during inspiration and increase with exhalation coincident with changes in intrathoracic pressure caused by respiratory muscle contraction including the diaphragm and chest wall and lung elastic recoil. These pressure indices have exaggerated increases in response to sudden perturbations in intrathoracic pressure that can result from exaggerated breathing, coughing, sneezing or straining, etc.

SUMMARY

Although changes in pressure, such as LAP, can indicate the onset of an adverse cardiac condition, such as congestive heart failure, some pressure changes occur in healthy people as well. For example, the inventors have discovered that during the course of a 24-hour period, such as a circadian cycle, LAP will typically both increase and decrease in healthy individuals. This is because during time of activity, such as walking, talking, moving, exercising, etc., the LAP increases to account for the physical demands placed on the individual's cardio-respiratory system. Similarly, during time of inactivity, such as sleeping, resting, meditation, etc., the LAP decreases due to the decrease in physical demand placed on the cardio-respiratory system. Therefore, it would be useful to have a system that considered the activity cycle of an individual when analyzing physiological or hemodynamic parameters, such as LAP.

Accordingly, there is a need for devices including implantable devices, systems and methods that monitor and analyze hemodynamic parameters to identify the onset of medical conditions, such as pulmonary edema and congestive heart failure, to allow clinical intervention as early as possible.

In one embodiment, a method of determining the status of an adverse cardiac condition of a medical patient is provided. The method includes: determining a series of first values of a hemodynamic parameter during a first period from a sensor implanted within the medical patient; determining a series of second values of the hemodynamic parameter during a second period from the sensor; calculating a first average value of the series of first values and a second average value of the series of second values; calculating a difference between the first average value and the second average value; and providing an indication of an adverse cardiac condition when the difference is less than a first predetermined threshold value.

In one embodiment, the first and second periods correspond to non-overlapping portions of a circadian rhythm, and in another embodiment, the first and second periods correspond to first and second circadian amplitudes. In one embodiment, the first period comprises a day time and the second period comprises a nighttime.

In one embodiment, the providing an indication of an adverse cardiac condition occurs three days after determining a first data point in the series of first values. In one embodiment, the adverse cardiac condition comprises a heart failure exacerbation, an acute cardiac event, heart failure, or pulmonary edema.

In other embodiments, the hemodynamic parameter comprises a left atrial pressure of the patient's heart, a cardiac impedance of the patient's heart, a cardiac output of the patient's heart, or a stroke volume of the patient's heart.

In one embodiment, the first predetermined threshold value is in a range of about 30-50% of a historical variation of the patient. In another embodiment, the first predetermined threshold value is in a range of about 50-70% of a historical variation of the patient.

In yet another embodiment, the method also includes: calculating a mean value of the first average value and the second average value; and providing an indication of an adverse cardiac condition when the difference is less than a first predetermined threshold value and the mean value is greater than a second predetermined threshold.

In one embodiment, the second predetermined threshold value is in a range of about 18-22 mm Hg. In another embodiment, the second predetermined threshold value is in a range of about 23-27 mm Hg.

In yet another embodiment, a method of determining the status of an adverse cardiac condition of a medical patient is provided. In one embodiment, the method includes: determining a first value of a hemodynamic parameter during a first time period, wherein said first value is based on information received from a sensor implanted in the medical patient; determining a second value of the hemodynamic parameter during a second time period, wherein said second value is based on information received from the sensor implanted in the medical patient; calculating a difference between the first and second values; and providing an indication of an adverse cardiac condition when the difference is less than a predetermined threshold value.

In one embodiment, the sensor comprises a pressure transducer, and said hemodynamic parameter comprises left atrial pressure. In another embodiment, said sensor comprises one or more electrodes, and said hemodynamic parameter comprises cardiac impedance.

In yet another embodiment, a method of determining the status of an adverse cardiac condition of a medical patient is provided. In one embodiment, the method includes: determining a series of first values of a hemodynamic parameter during a first period from a sensor implanted within the medical patient; determining a series of second values of the hemodynamic parameter during a second period from the sensor; calculating a first average value of the series of first values and a second average value of the series of second values; calculating a mean value of the first average value and the second average value; and providing an indication of an adverse cardiac condition when the mean value is greater than a predetermined threshold.

In yet another embodiment, an apparatus for treating cardiovascular disease in a medical patient is provided. The apparatus includes: a housing configured to be implanted within a medical patient; an implantable sensor, operable to generate a sensor signal indicative of a hemodynamic parameter of the medical patient; at least one implantable lead having a proximal end and a distal end, the implantable lead coupled to the implantable housing at the proximal end and coupled to the sensor at the distal end; a signal processor located within the housing, the signal processor operable to monitor circadian variations in the hemodynamic parameter of a medical patient and determine an occurrence of an adverse cardiac condition based upon a change in the circadian variations over a predetermined time period.

In one embodiment, the hemodynamic parameter comprises left atrial pressure of the medical patient's heart, a cardiac impedance of the patient's heart, a cardiac output of the patient's heart, or a stroke volume of the patient's heart. In one embodiment, the sensor is intended to be positioned within the heart. In another embodiment, the implantable sensor comprises a pressure transducer or an electrode.

In yet another embodiment, an apparatus for treating cardiovascular disease in a medical patient is provided. The apparatus includes: a housing configured to be implanted within the medical patient; an implantable sensor, operable to generate a sensor signal indicative of a hemodynamic parameter in the medical patient; at least one implantable lead having a proximal end and a distal end, the implantable lead coupled to the implantable housing at the proximal end and coupled to the sensor at the distal end; a signal processor located within the housing, the signal processor operable to receive the sensor signal from the implantable sensor and generate a processor output indicative of the difference between a first mean value of the sensor signal during a first time period and a second mean value of the sensor signal during a second time period; and a signaling device, operable to generate a health signal indicative of a cardiac condition, wherein said health signal is based at least in part on comparing the processor output to a predetermined value.

In one embodiment, the hemodynamic parameter comprises left atrial pressure of the medical patient's heart, a cardiac impedance of the patient's heart, a cardiac output of the patient's heart, or a stroke volume of the patient's heart.

In one embodiment, the first time period is the daytime and the second time period is the nighttime. In another embodiment, the implantable sensor is intended to be positioned within the heart. In another embodiment, the implantable sensor comprises a pressure transducer or an electrode.

In yet another embodiment, an apparatus for treating cardiovascular disease in a medical patient is provided. The apparatus includes: a housing configured to be implanted within the medical patient; an implantable sensor, operable to generate a sensor signal indicative of a fluid pressure of a left atrium of the medical patient's heart; at least one implantable lead having a proximal end and a distal end, the implantable lead coupled to said implantable housing at the proximal end, the implantable lead coupled to said implantable sensor at the distal end; a signal processor located within the housing, the signal processor operable to receive the sensor signal from the implantable sensor and generate a LAP difference processor output indicative of the difference between a first value based on the sensor signal during a first daily time period and a second value based on the sensor signal during a second daily time period; and a signaling device, operable to generate a alarm signal indicative of an adverse cardiac condition, wherein said alarm signal is based at least in part on comparing the LAP difference processor output to a first predetermined value.

In one embodiment, the first predetermined value is in a range of about 30-50% of a historical variation of the medical patient. In another embodiment, the first predetermined value is in a range of about 50-70% of a historical variation of the medical patient.

In another embodiment, the processor is further operable to generate an average LAP value based on the first and second values; and the alarm signal is based at least in part on comparing the LAP difference processor output to a first predetermined value and comparing the average LAP value to a second predetermined value.

In another embodiment, the second predetermined value is in the range of 18-22 mm Hg. In another embodiment, the second predetermined value is in the range of 23-27 mm Hg.

BRIEF DESCRIPTION OF THE DRAWINGS

The structure and operation of the invention will be better understood with the following detailed description of embodiments of the invention, along with the accompanying illustrations, in which:

FIGS. 5A-D show hemodynamic data readings from patients having different cardiac conditions;

DETAILED DESCRIPTION OF THE PREFERRED EMBODIMENTS

Figure 1A:
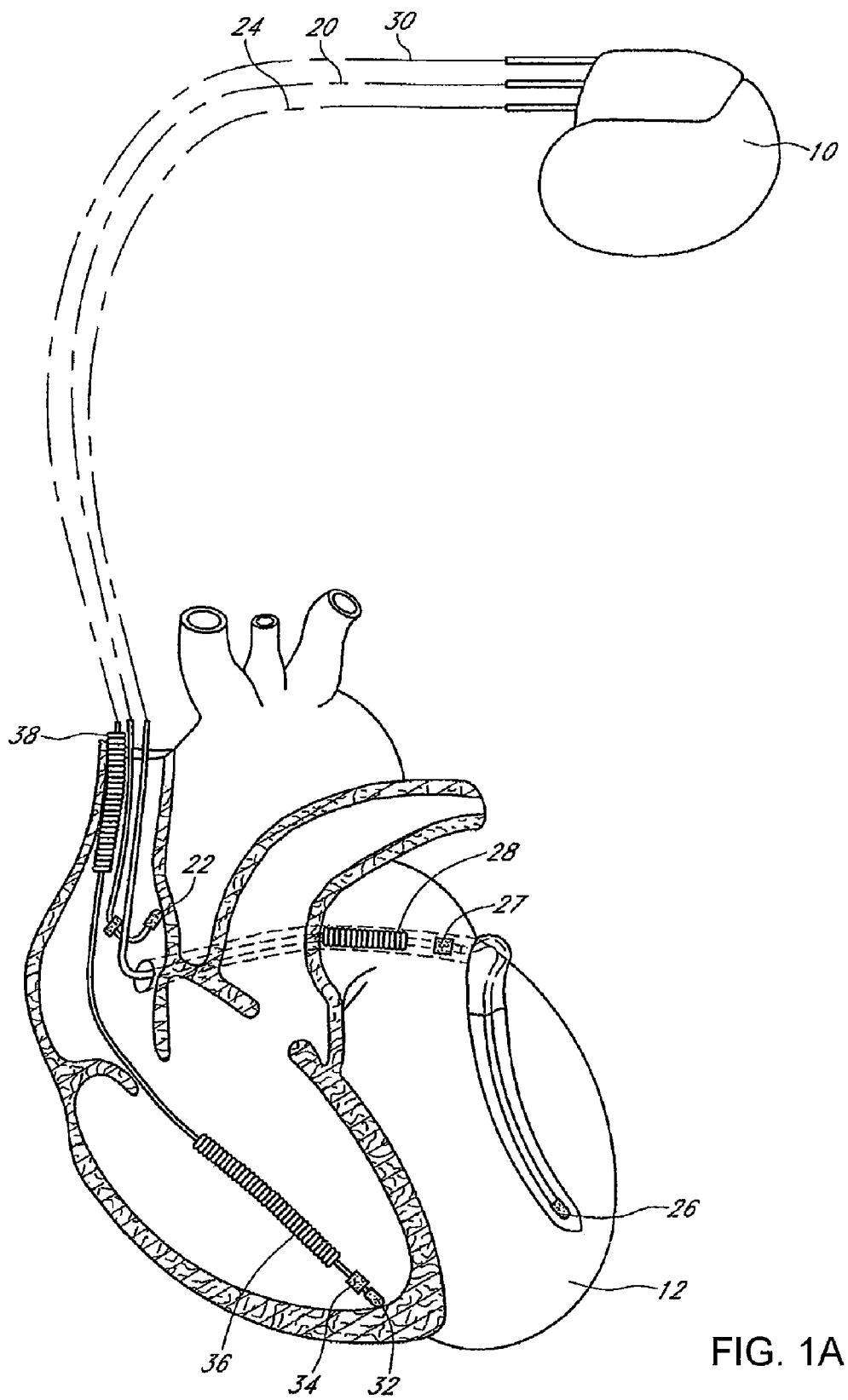
FIG. 1A is a simplified diagram illustrating a therapeutic appliance with an implantable stimulation device in electrical communication with at least three leads implanted into a patient's heart for delivering multi-chamber stimulation and shock therapy and a mechanical structural support to restrain excessive distension of the heart.

In various embodiments of the present invention, one or more hemodynamic parameters are monitored to provide an indication of the onset of an adverse cardiac condition. The monitored hemodynamic parameter can include any one or more of the following parameters: left atrial pressure, cardiac output, core temperature, cardiac impedance, stroke volume, blood pressure, heart rate, cardiac dyssynchrony or asynchrony (mechanical or electrical), ejection fraction, atrial volume, ventricular volume, as well as other physiological parameters of a patient. The adverse cardiac conditions that can be indicated, or diagnosed, by the monitoring of the hemodynamic parameters listed above include, but are not limited to, heart failure, congestive heart failure, acute congestive heart failure, pulmonary edema, as well as several others. The phrase "an cardiac adverse condition" as used herein, shall be given its ordinary meaning and shall include unfavorable or undesired illnesses, conditions, events, and episodes.

In several embodiments, one or more hemodynamic parameters are monitored with an implantable sensor coupled to an implantable device. In some embodiments, the implantable sensor is an electrode. In one embodiment, the sensor comprises a lead. In another embodiment, the sensor comprises a conductive material (e.g., at the surface) that detects changes in electrical potential at or near the sensor. For example, in several embodiments, the sensor can be used to determine a bioelectrical parameter, such as impedance, resistance, capacitance, voltage, current, etc. In some embodiments, the sensor can both detect electrical signals and pressure. In other embodiments, the sensor can detect electrical signals and/or pressure, and deliver electrical signals (e.g., pacing or defibrillation pulses) to the patient.

In some embodiments, the data generated by the sensor within the patient is communicated to a processor that is also included in the implantable device. For example, in one embodiment, an implantable device includes a microprocessor that is in communication with a pressure sensor or transducer that measures the fluid pressure within the left atrium of the heart. The pressure signal that is sensed by the sensor or transducer is provided to a processor located within the implantable device, which can store the data within the patient inside of an electronic memory.

The implantable device can include any of a variety of implantable devices known to those of skill in the art. For example, several implantable devices are described in U.S. Pat. Nos. 6,328,699 and 6,970,742, as well as U.S. application Ser. Nos. 10/438,309, filed May 13, 2003, published as U.S. Publication No. 2004/0106874, 11/111,691, filed Apr. 21, 2005, published as U.S. Publication No. 2005/0288596, and 11/015,336, filed Dec. 17, 2004, published as U.S. Publication No. 2005/0165456, all of which are incorporated by reference herein. In addition, the implantable device can include an implantable stimulation device, such as any of those discussed below.

Several advantages are realized by using an implantable device, according to some of the embodiments described herein. For example, in many cases, an implantable device can provide a more accurate measurement of a physiological parameter of a patient. In addition, an implantable device can often directly measure a physiological parameter, whereas non-implanted devices typically have to infer, or calculate the physiological parameter based upon a measurable value and a relationship that estimates the physiological parameter based upon the value of the measurable variable.

Implantable devices may also be more sensitive, have finer resolution, have a faster response time, and/or can assess physiological parameters and determine the status of a patient's health over a shorter time frame. The implantable device may also assess heart failure exacerbations over short time periods. For example, in some embodiments, the implantable device can assess adverse cardiac conditions in days as opposed to weeks.

In one embodiment, sensing is done entirely within the body. In other words, no sensors are located externally. For example, in one embodiment, the sensor is not a blood pressure cuff. However, in other embodiments, external sensors are used alone or in combination with internally implanted sensors. For example, one advantage to measuring left atrial pressure as compared to arterial blood pressure is the sensitivity of the absolute value changes.

Because LAP is typically in the range of 5-10 mm Hg, a change of 5 mm Hg in LAP can be an indicator of an adverse cardiac condition. However, since arterial blood pressure is typically in the range of 90-140 mm Hg, a change of 5 mm Hg in arterial blood pressure may not indicate a clinically significant event. Also, LAP and arterial pressure may produce different, and sometimes, opposite results. For example, in some situations, the circadian variation in LAP may increase, while the variation in arterial blood pressure may decrease. In other words, LAP and arterial blood pressure may trend in different directions. For example, the following data taken from an animal study illustrates that LAP and arterial pressures can trend differently.

tion. For example, the data show that prior to fluid overload exacerbation, systolic LAP and arterial pressure are 16.02 mm Hg and 111.76 mm Hg, respectively; but after fluid overload exacerbation, systolic LAP and arterial pressure both increase to 32.69 mm Hg and 127.83 mm Hg, respectively.

In addition, A. C. Guyton & A. W. Lindsey, in their article titled, "Effect of Elevated Left Atrial Pressure and Decreased Plasma Protein Concentration on the Development of Pulmonary Edema," 7 Circulation Research 649-57 (1959), which is incorporated by reference herein, show that LAP can be a good prognosticator of heart failure trends. If the arterial pressure does not always trend in the same direction as the LAP, then it cannot be successfully used as a reliable predictor of HF trends. Therefore, some of the limitations shown by Giles, et al. in "Circadian Variation in Blood Pressure and Heart Rate in Nonhypertensive Congestive Heart Failure," 28(6) J. Cardiovascular Pharmacology 733-40 (December 1996) are not surprising. In one embodiment, to ensure successful HF trending, hemodynamic parameters, such as those described herein, are monitored and trended using internally implanted devices.

A Valsalva maneuver is generally a maneuver to artificially increases the LAP to high values so other features and/or

| LVTip-RATip Sensor | Baseline | | Valsalva | | Atrial Tachycardia | | Ventricular Tachycardia | |
|---|---|---|---|---|---|---|---|---|
| | LAP | Arterial Pressure | LAP | Arterial Pressure | LAP | Arterial Pressure | LAP | Arterial Pressure |
| Waveform Feature | | | | | | | | |
| Cycle length (msec) | 371.65± 4.03 | 371.65± 4.03 | 356.69± 40.10 | 356.69± 40.10 | 234.52± 2.83 | 234.52± 2.83 | 234.23± 3.84 | 234.23± 3.84 |
| Systolic pressure (mm Hg) | 16.02± 2.20 | 111.76± 1.35 | 33.59± 1.59 | 84.19± 6.89 | 33.76± 3.97 | 89.08± 6.74 | 31.70± 5.88 | 62.61± 7.28 |
| Diastolic pressure (mm Hg) | 7.96± 1.71 | 91.77± 1.08 | 26.43± 0.73 | 65.49± 4.27 | 10.48± 3.32 | 70.31± 2.98 | 17.32± 2.93 | 47.08± 2.65 |
| Fluid overload exacerbation | | | | | | | | |
| Cycle length (msec) | 333.43± 3.86 | 333.43± 3.86 | 323.96± 79.31 | 323.96± 79.31 | 234.38± 0.71 | 234.38± 0.71 | 234.38± 0.70 | 234.38± 0.70 |
| Systolic pressure (mm Hg) | 32.69± 1.75 | 127.83± 2.71 | 55.31± 0.87 | 103.54± 10.04 | 39.21± 2.76 | 122.40± 4.60 | 38.60± 4.20 | 67.89± 7.94 |
| Diastolic pressure (mm Hg) | 22.82± 1.79 | 113.18± 2.18 | 47.20± 1.28 | 87.23± 8.16 | 23.48± 3.37 | 104.61± 4.11 | 26.58v 1.70 | 51.84± 4.48 |

The above data show that depending upon the condition of the patient, LAP and arterial pressure sometimes move in opposite directions. The four conditions listed above correspond to measurements made during (1) a baseline state, which is prior to an event or condition occurring, (2) a Valsalva maneuver, (3) atrial tachycardia, and (4) ventricular tachycardia. The pressures are measured both before and after fluid overload exacerbation.

The data show that in some conditions LAP increases while arterial pressure decreases. For example, prior to fluid overload exacerbation, systolic LAP and arterial pressure are 16.02 mm Hg and 111.76 mm Hg, respectively; however, during Valsalva, systolic LAP increases to 33.69 mm Hg, but systolic arterial pressure decreases to 84.19 mm Hg. In other situations, LAP and arterial pressure move in the same direccharacteristics of a cardiac monitoring or treatment apparatus or method can be tested and/or characterized. The maneuver can be self-induced, for example, by the patient, or performed on the patient. In some cases, the patient's airways are closed and the pressure in the lungs is raised to about 40 mm Hg. For example, during the study that yielded the above data, pressure was applied to the thorax to equalize the pressure in the lungs. Since the left atrium is located approximately between lungs and chest, equalizing the two pressures forces the LAP to rise to about the same amount, which is 40 mm Hg.

In several embodiments, the detection of an adverse condition is determined by monitoring a hemodynamic parameter over time. For example, an increasing or decreasing value of a hemodynamic parameter may be used to diagnose an adverse cardiac condition. Alternatively, the difference or delta between a hemodynamic parameter monitored at two time periods may be used to diagnose an adverse cardiac condition.

The period over which variations in parameter values occur can be selected as desired. In some embodiments, changes in a hemodynamic parameter from a daytime period to a nighttime period are monitored. However, in other embodiments, changes in hemodynamic parameters are monitored over periods corresponding to a patient's circadian rhythm. The term "circadian rhythm" is a broad term intended to have its ordinary meaning. In some embodiments, a circadian rhythm is a roughly 24-hour cycle in the physiological processes of living beings. The circadian rhythm can be described as having non-overlapping portions, such as consecutive periods of time. For example, for any given 24-hour period, two consecutive 12-hour period can be considered non-overlapping portions of a circadian cycle. However, the non-overlapping portions can have different durations. For example, a first period of a circadian rhythm can correspond to the hours of daylight in a day, and a second period of a circadian rhythm can correspond to the hours of darkness in the same day.

Monitoring based upon circadian variations or circadian rhythms is advantageous because some physiological and/or hemodynamic parameters, such as LV ejection fraction, exercise or effort capacity, or heart rate, etc., vary with a circadian cycle, and not only with a daytime/nighttime cycle. By monitoring based upon a circadian cycle the systems and devices as described herein can sometimes provide more accurate results. In addition, in some cases, variations in a physiological or hemodynamic parameter can occur more than once a day.

In one embodiment, an adverse cardiac condition is determined by comparing the daytime and night time values of a hemodynamic parameter. The change in a physiological parameter value, such as a hemodynamic parameter, from daytime to nighttime is sometimes referred to as a circadian change, a circadian rhythm, or a circadian variation. In some cases, the change in a physiological parameter is sometimes referred to as a daily change, a daily rhythm, or a daily variation.

In one embodiment, an implanted device monitors a patient's left atrial pressure (LAP) throughout the day and determines a mean LAP value of the patient during the daytime, and a mean LAP value of the patient during the nighttime. In one embodiment, mean daytime LAP corresponds to the average daytime LAP of the patient, and mean nighttime LAP corresponds to the average nighttime LAP of the patient.

In a healthy patient, the difference between the mean daytime LAP and the mean nighttime LAP should be about in a range of about 5 to 10 mm Hg. In addition, in a healthy patient, the mean daytime LAP should be less than the mean nighttime LAP. In addition, in a healthy patient, the mean daytime LAP should be less than about 15-20 mm Hg.

The difference between mean daytime LAP and mean nighttime LAP can decrease in a patient when there is a decrease in cardiac output from the left ventricle. In such situations, the mean nighttime LAP values approach or reach the mean daytime LAP values. This decrease in the difference between mean daytime LAP and mean nighttime LAP, in one embodiment, is an indication of an adverse cardiac condition, such as acute congestive heart failure (CHF) or pulmonary edema.

Therefore, in some embodiments, the methods and apparatus described herein are used to monitor the difference between mean daytime LAP and mean nighttime LAP values to determine the onset of acute CHF. Additional details regarding the devices, systems and methods of several of the various embodiments of the present invention are provided in greater detail below.

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

As shown in FIG. 1A, there is a stimulation device 10 in electrical communication with a patient's heart 12 by way of three leads 20, 24 and 30, suitable for delivering multi-chamber stimulation and shock therapy. The stimulation device 10 is coupled to an implantable right atrial lead 20 which allows the device 10 to sense atrial cardiac and right atrial pressure signals, and to provide right atrial chamber stimulation therapy. The right atrial lead 20 has at least an atrial tip electrode 22, a right atrial ring electrode 25, and a right atrial pressure sensor 14. The atrial tip electrode 22, right atrial ring electrode 25, and right atrial pressure sensor 14 are typically implanted in the patient's right atrial appendage, as shown. In the illustrated embodiment, the right atrial pressure sensor 14 is disposed at the atrial tip electrode 22. In other embodiments, the right atrial pressure sensor 14 may be located at other locations in the right atrial appendage. For example, the right atrial pressure sensor 14 may be positioned near or in the superior vena cava (SVC) such as near the SVC coil electrode 38.

The stimulation device 10 is coupled to a coronary sinus lead 24, which is designed for placement in the coronary sinus region via the coronary sinus ostium (OS). The coronary sinus lead 24 works with the simulation device 10 to sense left atrial and ventricular cardiac signals, sense left atrial pressure signals, and provide left chamber pacing therapy. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals. Furthermore, the coronary sinus lead 24 is designed to receive left atrial pressure signals using a left atrial pressure sensor 16. Additionally, the coronary sinus lead 24 is configured to deliver left ventricular pacing therapy using at least a left ventricular tip electrode 26, deliver left atrial pacing therapy using at least a left atrial ring electrode 27, and/or deliver shocking therapy using at least a left atrial coil electrode 28. For a complete description of a coronary sinus lead, see U.S. patent application Ser. No. 09/196,898, "A Self-Anchoring Coronary Sinus Lead" (Pianca et al.), and U.S. Pat. No. 5,466,254, "Coronary Sinus Lead with Atrial Sensing Capability" (Helland), which are hereby incorporated herein by reference.

Figure 1B:
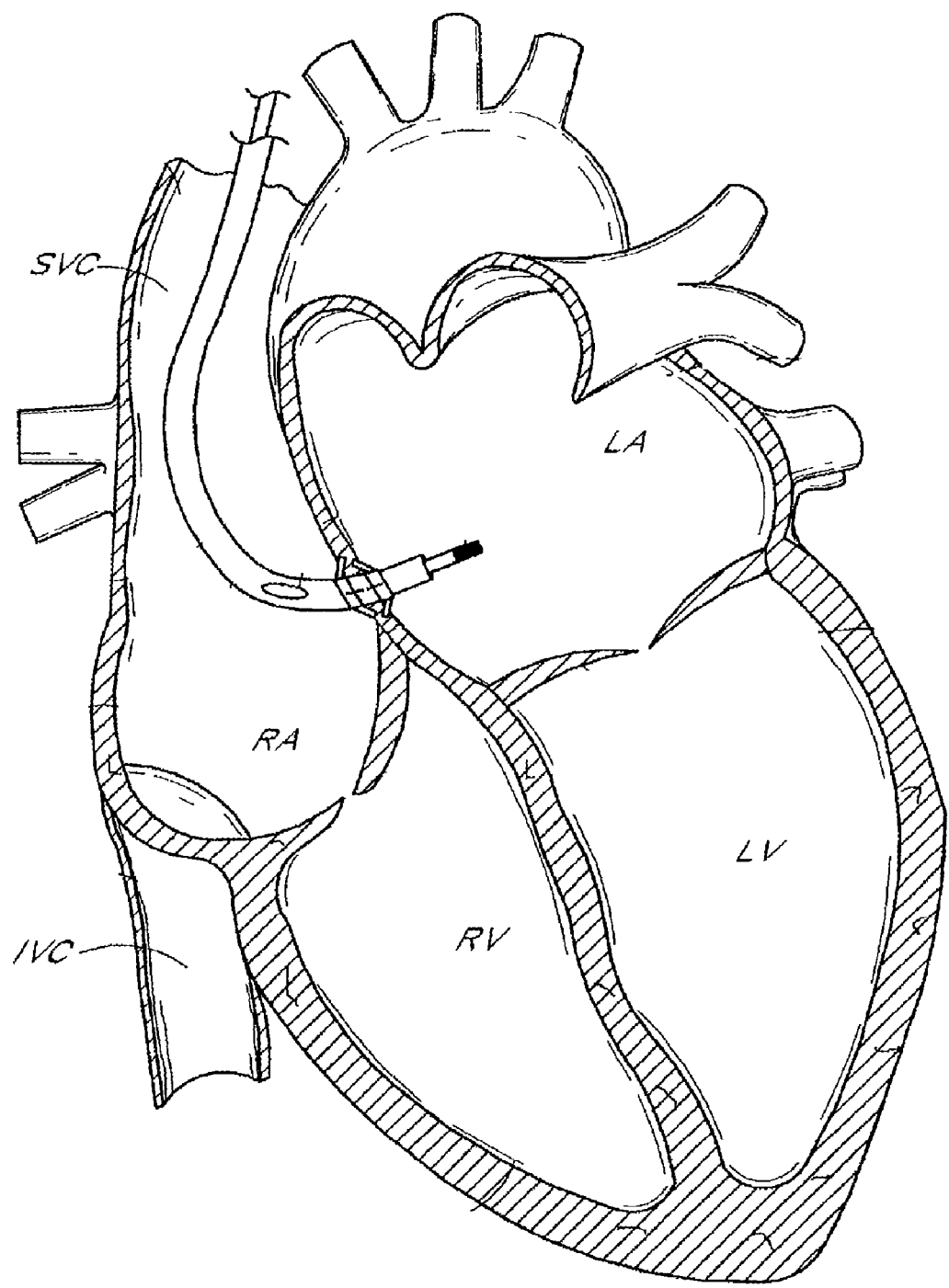
FIG. 1B is another simplified diagram illustrating a therapeutic appliance with an implantable stimulation device and a pressure sensor implanted into a patient's heart.

In the illustrated embodiment of FIGS. 1A and 1B, the left atrial pressure sensor 16 is disposed such that it is in contact with the septum wall and can thus measure fixated pressure. In one embodiment, the pressure sensor 16 is wedged in the atrial septal wall at the approximate location of the fossa ovalis. The pressure sensor 16 faces the blood of the left atrium, although it penetrates the septum from the right atrium.

The stimulation device 10 is also in electrical communication with the patient's heart 12 by way of an implantable right ventricular lead 30. In one embodiment, the right ventricular lead 30 includes a right ventricular tip electrode 32 connected to a right ventricular pressure sensor 18, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex. This causes the RV coil electrode to be positioned in the right ventricle and the SVC coil electrode 38 to be positioned in the superior vena cava.

Accordingly, the right ventricular lead 30 is capable of receiving cardiac signals and pressure signals, and delivering stimulation in the form of pacing and shock therapy to the right ventricle. In this embodiment, the right ventricular pressure sensor 18 is connected to the right ventricular tip electrode 32. In other embodiments, the right ventricular pressure sensor 18 may be disposed at other locations along the right ventricular lead 30. For example, the right ventricular pressure sensor 18 may be disposed near the end of the lead 30 or it may be disposed near the coil electrode 36.

Figure 2:
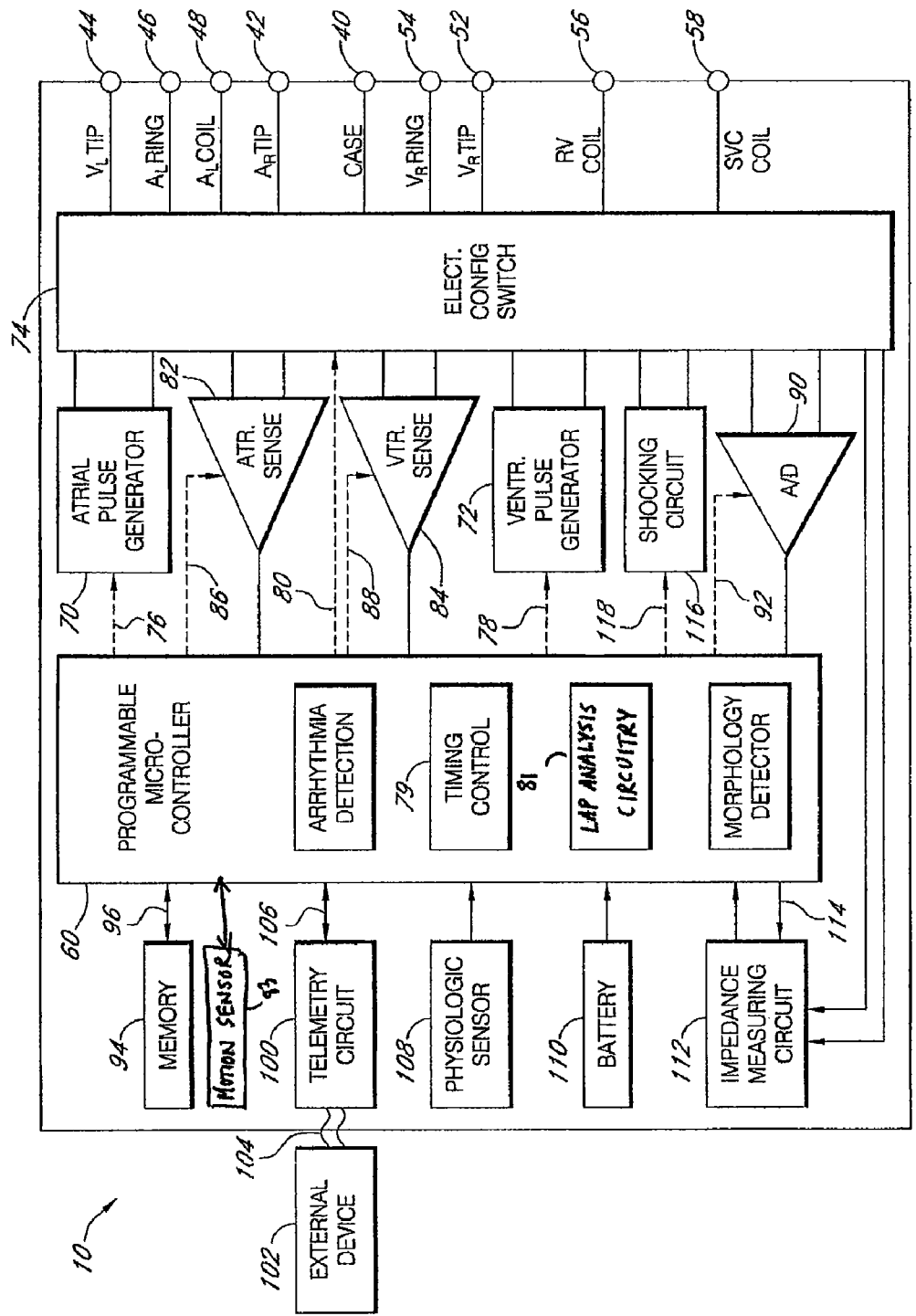
FIG. 2 is a functional block diagram of a multi-chamber implantable stimulation device of FIG. 1, illustrating the basic elements of a stimulation device which can provide cardioversion, defibrillation, and pacing stimulation, sense cardiac activity and pressure in four chambers of the heart and sense orientation of a patient.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the can, case, or case electrode and may be programmably selected to act as the return electrode for all unipolar modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, 58, 62, 64, and 66 (shown schematically and, for convenience, the names of the electrodes to which they are connected are shown next to the terminals). The connector includes at least a right atrial tip terminal (AR TIP) 42 adapted for connection to the atrial tip electrode 22 to achieve right atrial sensing and pacing.

The connector further includes at least a left ventricular tip terminal (VL TIP) 44, a left atrial ring terminal (AL RING) 46, and a left atrial shocking terminal (AL COIL) 48 to achieve left chamber sensing, pacing and shocking. The left ventricular tip terminal (VL TIP) 44, left atrial ring terminal (AL RING) 46, and left atrial shocking terminal (AL COIL) 48 are adapted for connection to the left ventricular ring electrode 26, the left atrial tip electrode 27, and the left atrial coil electrode 28, respectively.

The connector also includes a right ventricular tip terminal (VR TIP) 52, a right ventricular ring terminal (VR RING) 54, a right ventricular shocking terminal (RV COIL) 56, and an SVC shocking terminal (SVC COIL) 58 to support right chamber sensing, pacing and shocking, The right ventricular ring terminal (VR RING) 54, right ventricular shocking terminal (RV COIL) 56, and SVC shocking terminal (SVC COIL) 58 are adapted for connection to the right ventricular tip electrode 32, right ventricular ring electrode 34, the RV coil electrode 36, and the SVC coil electrode 38, respectively.

The connector further includes at least a right atrial pressure sensing terminal (RAP) 62, a left atrial pressure sensing terminal (LAP) 64, and a right ventricular pressure sensing terminal (RVP) 66 to achieve pressure sensing. The right atrial pressure sensing terminal (RAP) 62, left atrial pressure sensing terminal (LAP) 64, and right ventricular pressure sensing terminal (RVP) 66 are adapted for connection to the right atrial pressure sensor 14, the left atrial pressure sensor 16, and the right ventricular pressure sensor 18.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, noise detection windows, evoked response windows, alert intervals, marker channel timing, etc., which is well known in the art.

The microcontroller 60 also includes LAP analysis circuitry 81 which is used to keep track of hourly LAP values, determine mean LAP values for a patient for daytime and nighttime phases, analyze the delta between the mean values, and detect and/or analyze trends in the mean LAP values in order to detect risk for CHF, as discussed further below. The microcontroller 60 is also in communication with a motion sensor 83, as discussed further below.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the sensing polarity of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, is able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical or a pressure signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Electrical cardiac signals are also applied to the inputs of an analog-to-digital (ND) data acquisition system 90. The data acquisition system 90 is coupled to the right atrial lead 20, the coronary sinus lead 24, and the right ventricular lead 30 through the switch 74 to sample cardiac signals across any pair of desired electrodes. The data acquisition system 90 is configured to acquire IEGM signals, convert the raw analog data into digital signals, and store the digital signals for later processing, telemetric transmission to an external device 102, and/or further processing by an IEGM monitoring circuit 81.

The data acquisition system 90 may be coupled to the microcontroller 60 and the IEGM monitoring circuit 81, or other detection circuitry, for detecting an evoked response from the heart 12 in response to an applied stimulus, thereby aiding in the detection of capture. Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

Capture detection may occur on a beat-by-beat basis or on a sampled basis. Preferably, a capture threshold search is performed once a day during at least the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The implementation of capture detection circuitry and algorithms are well known. See for example, U.S. Pat. No. 4,729,376 (Decote, Jr.); U.S. Pat. No. 4,708,142 (Decote, Jr.); U.S. Pat. No. 4,686,988 (Sholder); U.S. Pat. No. 4,969,467 (Callaghan et al.); and U.S. Pat. No. 5,350,410 (Mann et al.), which are hereby incorporated herein by reference. The type of capture detection system used is not critical to the present invention.

Generally, if a capture is not detected after applying an electrical stimulus, at least one other electrical stimuli is applied to the heart immediately thereafter to prevent occurrence of cardiac arrhythmias. In some embodiments, depending on the characteristics of the cardiac signals sensed, certain parameters of the electrical stimulus that will be applied to the heart may be changed. For example, voltage may be increased to produce a more effective shock.

In addition to detecting capture, the microcontroller 60 includes an IEGM monitor 81 for receiving and monitoring the IEGM signals to detect possible abnormalities in the cardiac signals. The IEGM monitor 81 is coupled to and can receive IEGM signals from the data acquisition system 90. The IEGM monitor 81 then analyzes the IEGM signals by comparing the signals to stored parameters to detect substantial differences in amplitude, phase, waveshape, and/or other characteristics of the cardiac signal. The stored parameters are generally predetermined and may be input to the ICD by a physician or other clinician. Alternatively, the stored parameters may originate from the patient's own previously monitored cardiac activity.

The timing intervals between sensed events (e.g., P-waves, R-waves, and depolarization signals associated with fibrillation) may also be classified by the microcontroller 60 by comparing them to the predefined rate zone limit (e.g., bradycardia, normal, low rate VT, high rate VT, and fibrillation rate zones) and various other characteristics (e.g., sudden onset, stability, physiologic sensors, and morphology, etc.) to determine the type of remedial therapy that is needed (e.g., bradycardia pacing, anti-tachycardia pacing, cardioversion shocks or defibrillation shocks, collectively referred to as tiered therapy). Additionally, depending on the characteristics of the sensed signals, some parameters of electrical stimulus that will be applied to the heart may be changed. For example, in some instances, the voltage of the signal may be increased.

Differences between the waveform characteristics of the captured cardiac signal and the stored waveform parameters do not always, however, result from abnormalities and/or cardiac arrhythmias. Some differences, for example, result from the patient's physical activity or physical orientation. For example, the peak to peak amplitude of the IEGM signal may change by as much as 15% depending on the physical orientation of the patient. It is therefore advantageous for the stimulation device 10 to be able to detect abnormalities that are due to conditions other than abnormal conditions of the heart, so the device 10 does not respond improperly to these conditions.

In certain embodiments, a system and method to detect whether monitoring of a hemodynamic parameter is monitored during the day or during the night is provided. In one embodiment, the data regarding the hemodynamic parameter is processed in conjunction with a clock. Thus, as data is uploaded, the processor can distinguish if the data is "daytime data" or "nighttime data."

In other embodiments, daytime LAP readings may be distinguished from nighttime LAP readings using a motion sensor device 83 included in the stimulation device 10. One example of an implantable motion sensor device 83 that may be used with certain embodiments disclosed herein is disclosed in U.S. Pat. No. 6,773,404 titled "Discriminating Between an Awake Phase and a Sleep Phase of a Patient in an Active Implantable Medical Device" which is hereby incorporated in its entirety herein.

In certain embodiments, the motion sensor device 83 is an accelerometer. For example, with the accelerometer implanted in the patient, motion detected by the accelerometer may be processed to determine whether the patient is asleep or awake. A high level of activity sensed by the accelerometer may signal an awake state and a low level of activity sensed by the accelerometer may signal a sleep state, as a patient tends to move considerably less when asleep then when awake. Consequently, during phases where the accelerometer senses the patient is asleep, the stimulation device 10 categorizes LAP readings as nighttime readings. On the other hand, during phases where the accelerometer senses the patient is awake, the stimulation device 10 categorizes LAP readings as daytime readings.

In certain other embodiments, the readings from the motion sensor device 83 are identified as active phase or inactive phase readings, instead of daytime or nighttime readings. In certain embodiments, an implantable motion sensor device 83 is carried externally from the patient. For example, in some embodiments, the motion sensor device 83 is worn around the wrist or waist of the patient.

In other embodiments, daytime LAP readings are distinguished from nighttime LAP readings using a global positioning system (GPS), wherein movement detected using GPS locating features may be used to determine whether the patient is moving or stationary. In certain other embodiments, an atomic clock may be used to determine whether the LAP readings are taken during the daytime or the nighttime. In yet further embodiments, other devices may be used to classify LAP readings, for example, as daytime or nighttime readings, active or inactive readings, etc.

In certain embodiments, LAP measurements are taken periodically, according to a predetermined frequency or schedule. For example, in one embodiment, an implantable device takes LAP measurements hourly, every two hours, every four hours, every six hours, every twelve hours, or twice, four, six, eight, twelve, 16, 24, 48, or 96 times per day.

Figure 3:
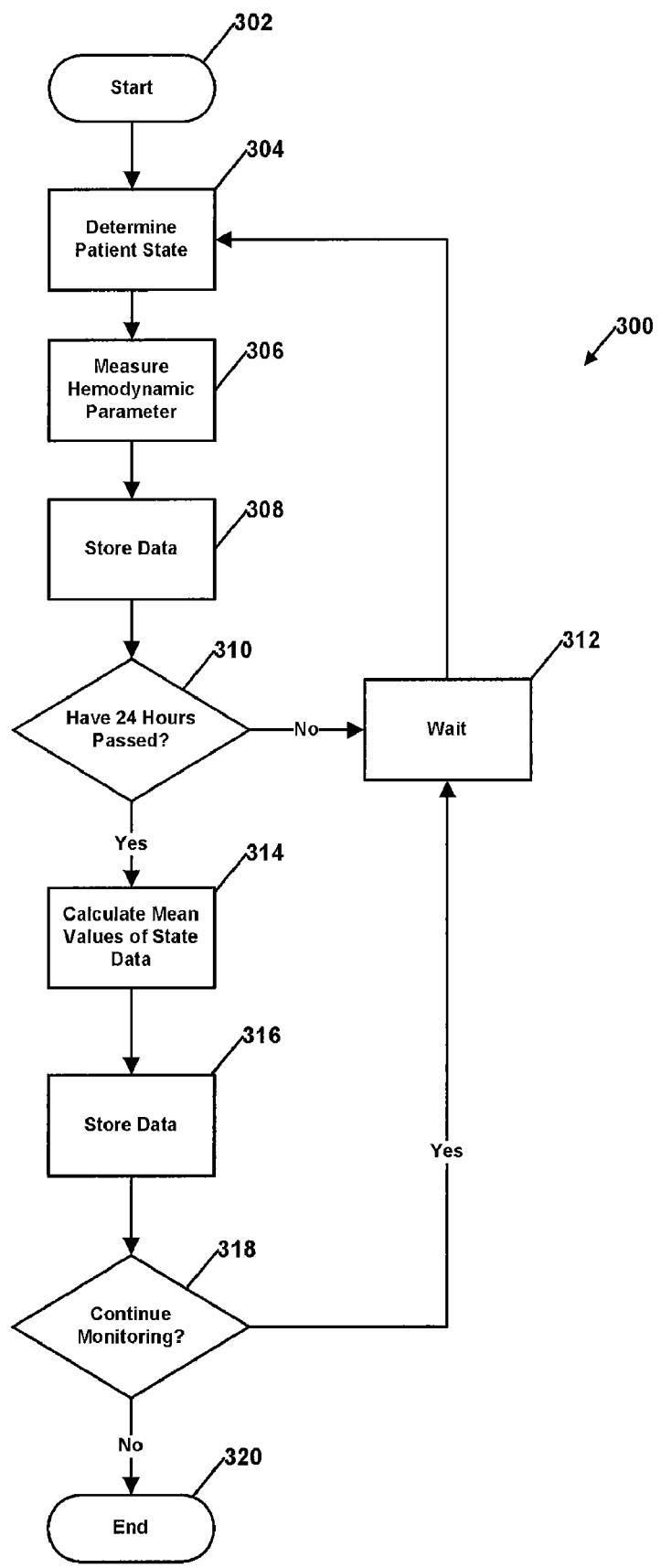
FIG. 3 illustrates a method of acquiring and storing hemodynamic parameter data according to certain embodiments of the invention.

FIG. 3 illustrates a method 300 of acquiring and storing hemodynamic parameter data in accordance with one embodiment of the present invention. The method 300 begins at step 302. At step 304, the method 300 determines the state of the patient. For example, at step 304, the method 300 determines whether it is daytime or nighttime for the patient. In another embodiment, at step 304, the method 300 determines whether the patient is active or inactive, such as exercising or at rest.

Any of a variety of devices can be used to determine whether the patient is active or inactive, such as any of the motion sensor 83 described above with respect to FIG. 2. For example, in some embodiments, an activity sensor includes an accelerometer implanted within the patient. The accelerometer generates a signal that varies with the movement of the patient, and in therefore can indicate whether the patient is in an active or inactive state. Based upon sensed activity, the accelerometer can be used to distinguish daytime from nighttime. In other embodiments, other devices are used as an activity sensor. For example, a clock, such as an atomic clock and/or a global positioning system can also be used to determine patient activity, as well as daytime from nighttime, as discussed above.

At step 306, the method 300 measures a desired hemodynamic parameter of the patient. For example, in one embodiment, the method 300 measures the LAP or an indication of LAP of the patient. In other embodiments, the method 300 determines the cardiac impedance, the core temperature, the ejection fraction, or the cardiac output of the patient. In yet other embodiments, the method 300 determines more than one hemodynamic parameter of the patient at step 306. The information determined by the method 300 is stored at step 308.

At step 310 the method 300 determines if the desired time period has passed. For example, in one embodiment, the method 300 determines if 24 hours have passed since the last hemodynamic parameter measurement. If not, the method 300 proceeds to step 312. At step 312 the method 300 waits a predetermined time period, such as one hour. The method 300 can alternatively wait any other desired time period, such as half an hour, two hours, four hours, six hours, twelve hours, etc. After the desired time period has passed, the method 300 returns to step 304.

If the desired time period has passed, the method 300 proceeds to step 314. At step 314 the method 300 calculates the mean value of the stored hemodynamic parameter data. In other embodiments, the method 300 saves stored hemodynamic parameter data, such as in a histogram, and calculates the median value or a few or selected maxima values. In some embodiments, the method 300 removes, ignores, or drops one or more maxima values prior to calculating mean values because it treats the maxima values as noise. For example, in one embodiment, the method 300 calculates a mean daytime LAP value and a mean nighttime LAP value at step 314. In other embodiments, the method 300 determines the maximum daytime LAP value and maximum nighttime LAP value. The calculated data is stored by the method 300 at step 316.

In other embodiments, the method 300 obtains hemodynamic parameter data during a predetermined period and then sorts, or stores the data, for example as a histogram. For example, in some embodiments, the method 300 obtains hemodynamic parameter data during a 24-period and then selects the maximum value and the minimum value to determine a circadian variation of the hemodynamic parameter. In other embodiments, a pre-determined number of maxima and minima are discarded and then the remaining maximum and minimum are selected to determine the circadian variation. For example, in some embodiments, the top and/or bottom 3%, 5%, or 10% of values are discarded or ignored prior to selecting the maximum and minimum to determine circadian variation. As discussed above, extreme values are sometimes discarded to account for noise that may have been introduced into the system.

At step 318, the method 300 determines if the method 300 is to continue hemodynamic parameter monitoring or not. If yes, the method 300 proceeds to step 312. If at step 318 the method 300 determines that it is not to continue hemodynamic parameter monitoring, the method 300 proceeds to step 320, where the method 300 ends.

Figure 4A:
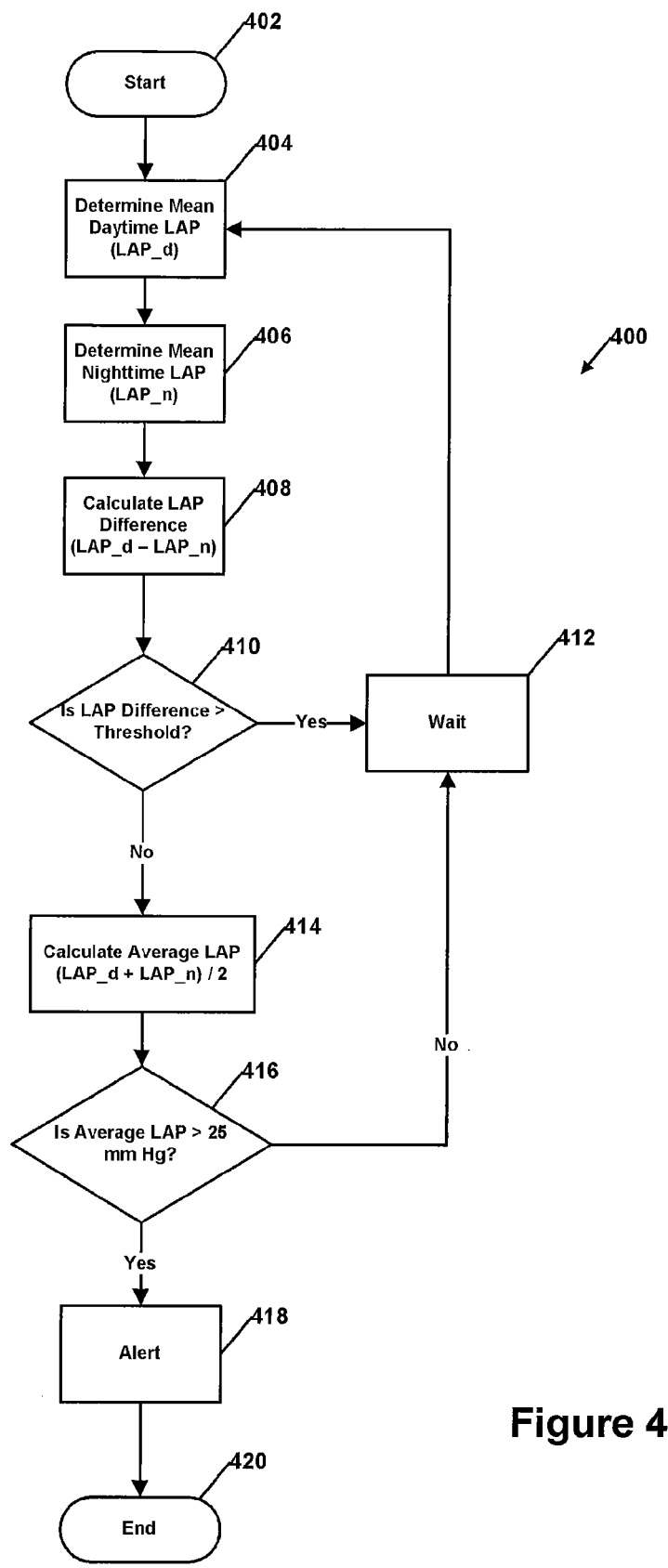
FIGS. 4A and 4B illustrate methods in accordance with other embodiments of the present invention, for monitoring a hemodynamic parameter to determine the onset of an adverse cardiac condition.

FIG. 4A illustrates a method 400 in accordance with another embodiment of the present invention, for monitoring a hemodynamic parameter to determine the onset of an adverse cardiac condition. For example, in the illustrated embodiment, the method 400 monitors a patient's mean daytime LAP value and mean nighttime LAP value to determine if a patient is at risk for CHF or pulmonary edema.

The method 400 begins at step 402. At step 404, the method 400 determines the mean daytime LAP (LAP_d), and at step 406 it determines the mean nighttime LAP (LAP_n). For example, in one embodiment, the mean daytime LAP and mean nighttime LAP are determined according to the method 300 discussed above with respect to FIG. 3.

At step 408, the method 400 calculates the LAP difference. For example, in one embodiment, the method 400 calculates the LAP difference as the difference between the mean daytime LAP and the mean nighttime LAP, such that:

$$\Delta\_LAP = LAP\_d - LAP\_n$$

In other embodiments, the method 400 calculates or determines a LAP difference by monitoring a histogram of LAP values, such as a 24-hour LAP histogram. The difference between minimum and maximum values of the histogram can be used to determine the LAP difference. In addition, in some cases the nighttime LAP can possibly exceed the daytime LAP value. For example, this can occur when heart failure becomes severe in its later stages and in supine position, blood accumulates in the chest instead of the peripheral vasculature. When this occurs, the method 400 determines a negative LAP difference. The method 400 treats a LAP difference less than zero as a minimum difference and proceeds accordingly.

At step 410, the method 400 determines if the LAP difference is greater than a threshold value. In various embodiments, the threshold value is 5, 8, 10, or 12 mm Hg. In other embodiments, the threshold value is about 30%, about 50%, about 70%, in the range of about 30-50%, or in the range of about 50-70% of the average circadian variation of the patient over a previous, predetermined time period. In some embodiments, the predetermined time period is a few days, in the range of about 1-5 days, in the range of about 1-3 weeks, or in the range of about 1-6 months.

The threshold value can be determined on patient-by-patient basis. In some embodiments, the threshold value is specific to each patient. For example, in some embodiments, an initial threshold value is determined. However, if the method 400 determines an alarm too frequently or infrequently, the threshold can be increased or decreased accordingly. In some embodiments, the threshold value is adjusted or programmed remotely, such as from a remote monitoring station operated by a clinician.

If the LAP difference is greater than the threshold value, the method 400 determines that the patient is not at risk for an adverse cardiac condition, and the method 400 continues to step 412. At step 412, the method waits a predetermined time period, such as any of the time periods discussed above. The method 400 then returns to step 404.

If the LAP difference is not greater than the threshold value, the method 400 continues to step 414. At step 414, the method calculates the average LAP, such that:

$$Average\_LAP = (LAP\_d + LAP\_n)/2$$

At step 416, the method 400 determines if the average LAP value is greater than a second threshold value. For example, in one embodiment, the method 400 determines if the average LAP value is greater than 25 mm Hg. If not, the method 400 determines that the patient is not at risk for an adverse cardiac condition and continues to step 412. If the average LAP value is greater than 25 mm Hg, the method determines that the patient is at risk for an adverse cardiac condition and continues to step 418.

Depending on other conditions of the patient, the threshold value could be less than 25 mm Hg. For example, in some situations, the threshold value is between 14 and 24 mm Hg, depending upon blood proteins or other elements of the patient's blood chemistry. Some patients suffering from other medical conditions will have a lower pressure threshold value because such patients could become sick or have the onset of congestive heart failure at a pressure over only 14 mm, at a pressure between 14 and 24 mm Hg, or at a pressure less than 25 mm Hg, in some cases. For example, depending upon the presence of certain peptides in the patient's blood, or the patient's blood chemistry, the threshold value could be less than 25 mm Hg. Such conditions are described by A. C. Guyton & A. W. Lindsey, in their article titled, "Effect of Elevated Left Atrial Pressure and Decreased Plasma Protein Concentration on the Development of Pulmonary Edema," 7 Circulation Research 649-57 (1959), which is incorporated by reference herein.

At step 418, the method 400 initiates an alarm. For example, in one embodiment, the method 400 causes an alarm signal to be provided to the medical patient. In other embodiments, the method 400 merely sets a data flag to an alarm state so a clinician or other user can become aware of the alarm condition during future analysis. The method 400 ends at step 420. The alarm signal, includes, but is not limited to, auditory, visual, electrical, and mechanical signals.

Figure 4B:
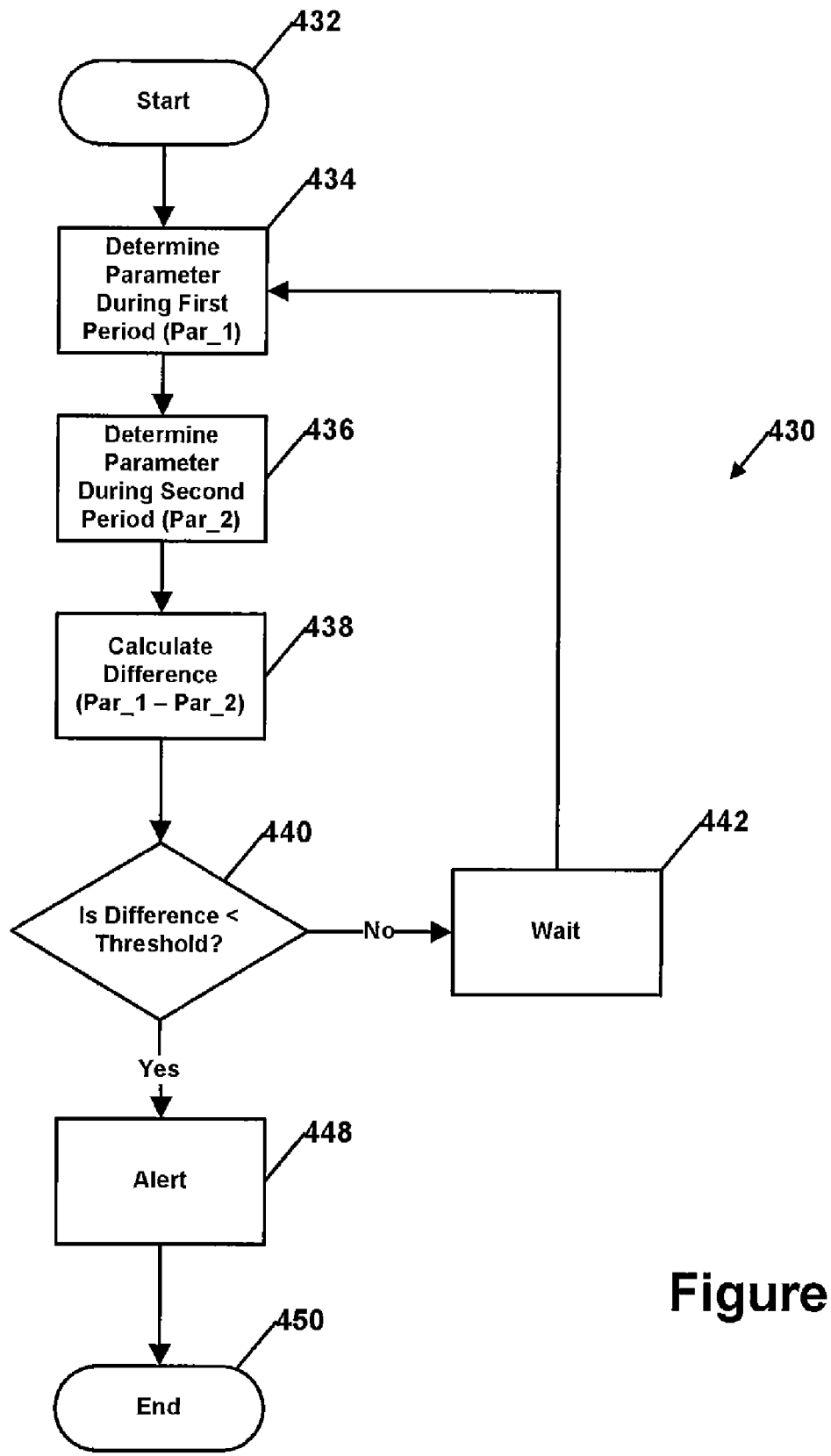

FIG. 4B illustrates a method 430 in accordance with another embodiment of the present invention, for monitoring a hemodynamic parameter to determine the onset of an adverse cardiac condition. For example, in the illustrated embodiment, the method 430 monitors circadian variation of a hemodynamic parameter, such as LAP, impedance, or any other hemodynamic parameter described herein, to determine if a patient is at risk for CHF or pulmonary edema.

The method 430 begins at step 432. At step 434, the method 430 determines a hemodynamic parameter value of a patient during a first time period. At step 436, the method 430 determines a hemodynamic parameter value of the patient during a second time period. In one embodiment, the first and second time periods correspond to non-overlapping portions of a circadian cycle. In another embodiment, the first and second time periods correspond to circadian amplitudes. In other embodiments, the first and second time periods define the circadian period of the patient. In yet other embodiments, the first time period corresponds to the day time, and the second time period corresponds to the night time.

At step 438, the method 430 determines the variation in the hemodynamic parameter. For example, in one embodiment, at step 438, the method 430 determines the difference between the hemodynamic parameter value during the first and second periods. At step 440, the method 430 determines if the variation is less than a predetermined threshold. The threshold can be programmed by a user or clinician, and can be specific to the medical patient. In other embodiments, the threshold is based upon clinical data from the patient or from a population. In other embodiments, the threshold is determined according to the method 450 described below.

If at step 440 the method 430 determines that the variation is not less than the threshold value, the method 430 proceeds to step 442. At step 442, the method waits a predetermined time period and then returns to step 434. For example, at step 442, the method 430 could wait about 24 hours. If at step 440 the method 430 determines that the variation is less than the threshold, the method 430 proceeds to step 444. At step 444 the method 430 generates an alarm, such as described herein. The method 430 then ends at step 446.

One embodiment of a method of determining a hemodynamic variation threshold value of a medical patient is illustrated in the method of FIG. 5C. The method 450 begins at step 452. At step 454 the method 450 determines if the patient's blood chemistry is normal. If yes, the method 450 proceeds to step 456. At step 456, the method 450 assigns or selects a threshold adjustment factor of about 0.7 and proceeds to step 460. If no, the method 450 proceeds to step 458. At step 458, the method 450 assigns or selects a threshold adjustment factor of about 0.3 and proceeds to step 460. At step 460, the method 450 determines a threshold value. In one embodiment, the method 450 determines the threshold value by multiplying a historical variation value with the threshold adjustment factor. For example, in one embodiment, at step 460, the method 450 multiplies a historical circadian variation value by a factor of 30% (if the patient has "abnormal" blood chemistry) or 70% (if the patient has "normal" blood chemistry). Additional details regarding the relationship between blood chemistry and hemodynamic parameter levels is discussed by A. C. Guyton & A. W. Lindsey, in their article titled, "Effect of Elevated Left Atrial Pressure and Decreased Plasma Protein Concentration on the Development of Pulmonary Edema," 7 Circulation Research 649-57 (1959), which is incorporated by reference above.

Hemodynamic parameter data from patients that are healthy, experiencing a worsening condition, such as the onset of an adverse cardiac condition, and experiencing an improving condition, such as the recovery from an adverse cardiac condition, are illustrated in FIGS. 5A, 5B, and 5C, respectively. In FIGS. 5A, 5B, and 5C, the unfilled circles represent daily mean daytime LAP values and the filled circles represent daily mean nighttime LAP values. The length of the line connecting each pair of mean daily daytime and nighttime LAP values represents the LAP difference for the given day. The midpoint of each line represents the average LAP value for each given day.

As discussed above, in one embodiment, in a healthy patient the mean daytime LAP is greater than the mean nighttime LAP, the LAP difference is relatively constant, and the average LAP value is less than 25 mm Hg. In one embodiment, the LAP difference is the difference between the mean daytime LAP value and the mean nighttime LAP value. However, it should be understood by those of skill in the art that the LAP difference in other embodiments is the difference between any given daytime LAP value and a nighttime LAP value.

For example, in other embodiments, the LAP difference is the difference between the maximum daytime and nighttime LAP values, minimum daytime and nighttime LAP values, or other such values. In one embodiment, the average LAP value is the average of the average daytime LAP value and the average nighttime LAP value for a given day. Other average LAP values can be utilized, similar to those discussed above with respect to the LAP difference. Data recorded with a hemodynamic parameter monitor that is coupled to such a healthy patient is illustrated in FIG. 5A.

In another embodiment, hemodynamic data from a patient with a worsening cardiac condition is illustrated in FIG. 5B. The LAP difference is decreasing over time, and the average LAP value is increasing. When the average LAP value exceeds a predetermined threshold, such as 25 mm Hg, the method, device, or system sends or sets an alarm, as discussed above.

Finally, in yet another embodiment, hemodynamic data from a patient with an improving cardiac condition is illustrated in FIG. 5C. In the improving patient, the LAP difference increases over time, and the average LAP value decreases. When the average LAP value falls below the predetermined threshold, such as 25 mm Hg, the method, device, or system sends or sets an alarm indicating improvement or recovery from the adverse cardiac condition.

Figure 4C:
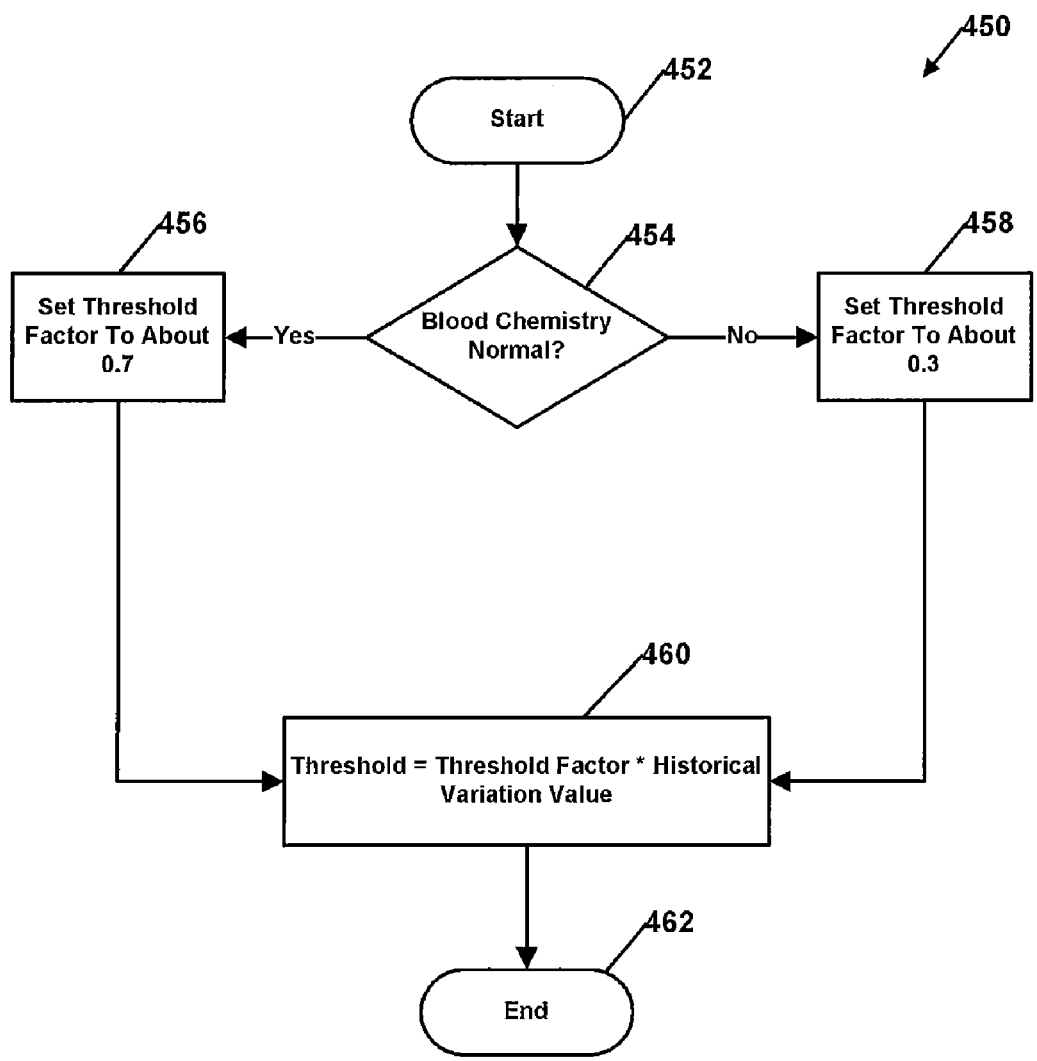
FIG. 4C illustrates a method of determining a threshold value of a patient in accordance with one embodiment of the present invention.

For example, in one embodiment, an implantable device performs the method 300 of FIG. 3 to determine that the mean nighttime LAP value of the first individual 502 for the twenty-four hour period shown in FIG. 5D is 10.4 mm Hg. The method 300 further determines that the mean daytime LAP value of the first individual 502 for the twenty-four hour period shown is 13.9 mm Hg. Then, using the method 400 of FIG. 4, the implantable device determines first individual's 502 LAP difference is 3.5 mm Hg (=13.9−10.4 mm Hg), and his average LAP value is 12.2 mm Hg. In one embodiment, the method 400 uses a LAP difference threshold of 3 mm Hg and an average LAP threshold of 25 mm Hg. Therefore, the method 400 concludes that an alert is not recorded by the implantable device because LAP difference of 3.5 mm Hg is greater than the LAP difference threshold value (3 mm Hg).

Similarly, in one embodiment, an implantable device coupled to a second individual 503 performs the method 300 of FIG. 3 to determine mean daytime and nighttime LAP values for the twenty-four hour period shown. The mean daytime LAP value is 27.3 mm Hg and the mean nighttime LAP value is 24.4 mm Hg. Then, using the method 400 of FIG. 4, the implantable device determines the second individual's 503 LAP difference is 2.9 mm Hg (=27.3−24.4), and the average LAP value is 25.8 mm Hg. In one embodiment, the method 400 also uses a LAP difference threshold of 3 mm Hg and an average LAP threshold of 25 mm Hg. Therefore, the method 400 concludes that an alert is recorded by the implantable device because the LAP difference of 2.9 mm Hg is less than the LAP difference threshold (3 mm Hg) and the average LAP of 25.8 mm Hg is greater than the average LAP threshold (25 mm Hg).

Figure 6:
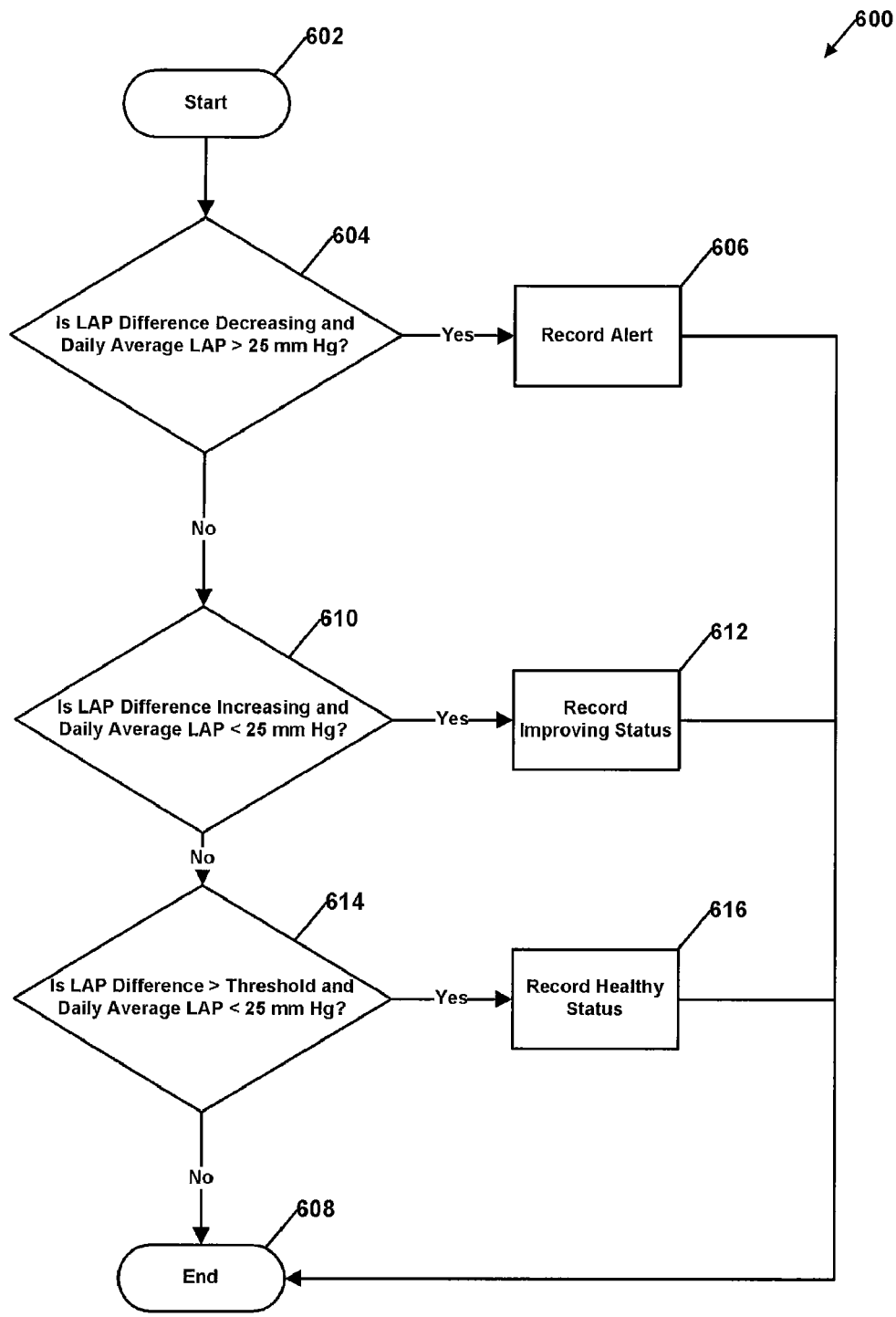
FIG. 6 illustrates a method for using hemodynamic parameter data to assess the condition of a patient at risk for CHP.

FIG. 6 illustrates another embodiment, in which a method 600 determines the status or condition of a medical patient at risk for an adverse cardiac condition. The method 600 beings at step 602.

At step 604, the method 600 determines if a patient's LAP difference is decreasing compared to a previous number of days, and further if the patient's most recent daily average LAP value is greater than a threshold value, such as 25 mm Hg. If so, the method 600 continues to step 606, where an alert is recorded in the stimulation device 10.

Figure 7A:
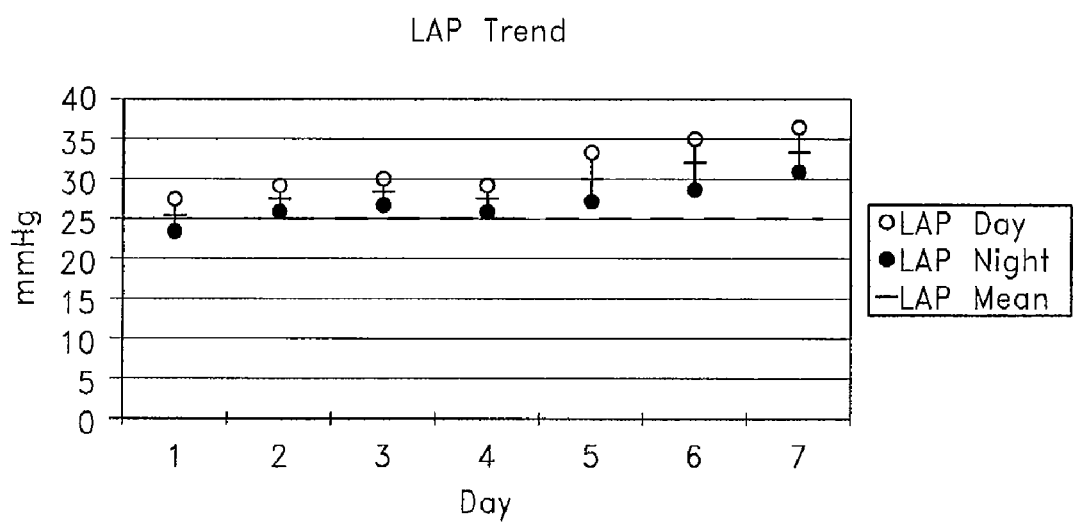
FIGS. 7A-7C show mean LAP value graphs over the course of several days for three patients.

For example, in FIG. 7A, the patient's LAP difference on day seven 701 is less than the average of the LAP differences for the two prior days 702 and 703, and furthermore the patient's daily average LAP on day seven 701 is greater than 25 mm Hg, noted by line 750. Consequently, at step 606, the method 600 records an alert. The method 600 then ends at step 608.

However, if at step 604 the conditions are not satisfied, the method 600 continues to step 610. At step 610, the method 600 checks to see if a patient's LAP difference is increasing compared a previous number of days, and further if the patient's most recent daily average LAP value is less than a threshold value, such as 25 mm Hg. If these conditions are satisfied, the method continues to step 612, where the method 600 records that the patient's status is improving.

Figure 7B:
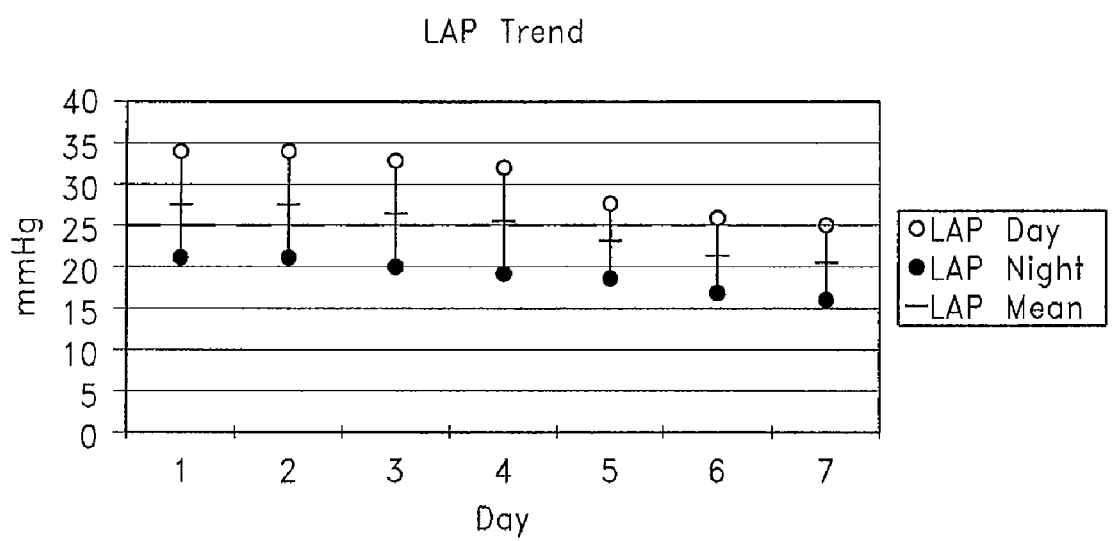

For example, in FIG. 7B, the patient's LAP difference on day seven 711 is greater than the average of the LAP differences for the two prior days 712 and 713, and furthermore the patient's daily average LAP on day seven 711 is less than 25 mm Hg, again noted by line 750. Consequently, the conditions of step 604 are not satisfied. As a result, since the conditions of step 610 are satisfied, the method 600 records that the patient's condition is improving at step 612. The method then ends at step 608.

However, if the conditions of step 610 are not satisfied, the method 600 continues to step 614. At step 614, the method 600 determines if LAP difference is greater than a threshold value and if the daily average LAP value is less than 25 mm Hg for a previous number of day. If these conditions are satisfied, the method 600 continues to step 616 where the method 600 records that the patient's status is healthy.

Figure 7C:
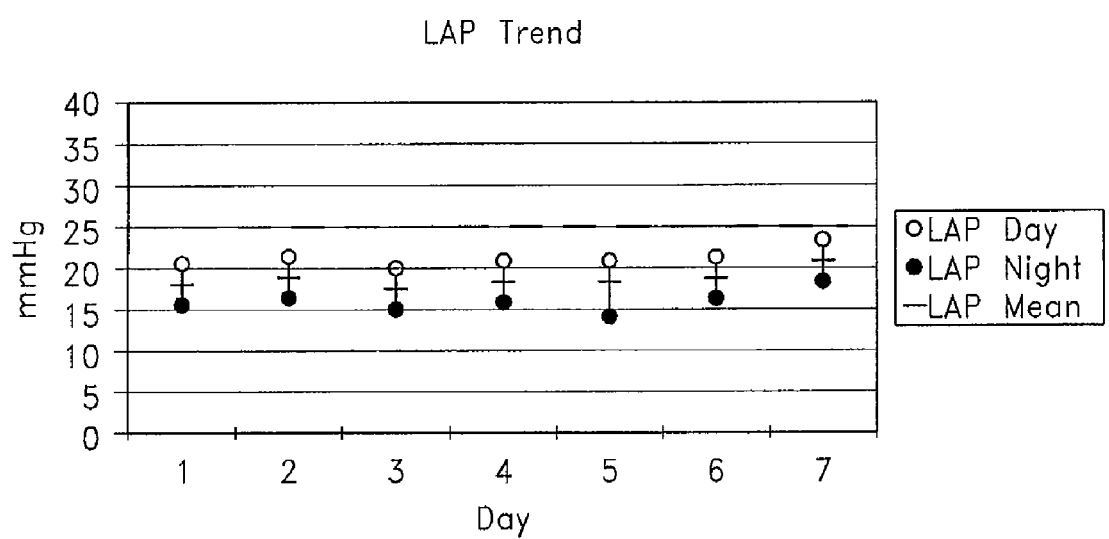

For example, in FIG. 7C, the patient's LAP difference value on days five 723, six 722, and seven 721 is less than a sample threshold value of 3 mm Hg, and also the patient's daily average LAP value for those same three days 721, 722 and 723 is less than 25 mm Hg, again noted by line 750. Therefore, the method 600 records that the patient's condition is healthy. The method then ends at step 608. If, however, the conditions of step 614 are not satisfied, the process 600 ends at step 608.

In other embodiments, the process determines when other combinations of conditions occur. For example, if the process determines that the delta is decreasing and mean lap is below 25, the process determines that either the patient's health is worsening, or that the patient is not moving around enough. For example, if the patient is not undertaking enough physical activity, this condition could occur. Therefore, in such cases, the process 600 uses another device, such as an accelerometer or any motion detector discussed herein to determine if the patient is moving around sufficiently.

In other embodiments, other hemodynamic parameters are similarly monitored to determine the onset or progression of an adverse cardiac condition. For example, in one embodiment, cardiac impedance is monitored to determine the occurrence of heart failure. Cardiac impedance is a measure of the ability of cardiac tissue to conduct an electric current. Impedance values include changes in the electrical conductivity of or within the heart.

In several embodiments, impedance is measured between locations within the body. In one embodiment, cardiac impedance is measured between two locations in the heart or between one location in the heart and one location outside of the heart. For example, in one embodiment, a first electrode is placed in the left ventricle and a second electrode is placed in the right ventricle. In another embodiment, a first electrode is placed in the heart (such as in a ventricle) and the second electrode is placed in a subcutaneous pocket in the shoulder area. Other locations may also be used. In addition to electrodes, other conductors may be used. More than two conductors may used in some embodiments to measure impedance between more than two locations.

In one embodiment, trends in the circadian rhythm of impedance can be used to diagnose an adverse cardiac condition. Similar to trends in LAP, described above, cardiac impedance changes within a period of about twenty-four hours. Thus, cardiac impedance, alone or together with LAP, can be used to detect or diagnose an adverse cardiac condition.

In one embodiment, an adverse cardiac condition is diagnosed when the peak-peak circadian variations in impedance decrease by more than a patient-specific threshold. In one embodiment, the threshold is about 30%. In other embodiments, the threshold is about 20%, 40% or 50%. In another embodiment, a smaller delta, or peak-to-peak circadian variation, in combination with a decreasing trend in the average impedance values are used to detect an adverse cardiac condition. In yet another embodiment, the average impedance values are used to detect an adverse cardiac condition, alone or in combination with other impedance values, such as cardiogenic impedance trends.

Figure 8:
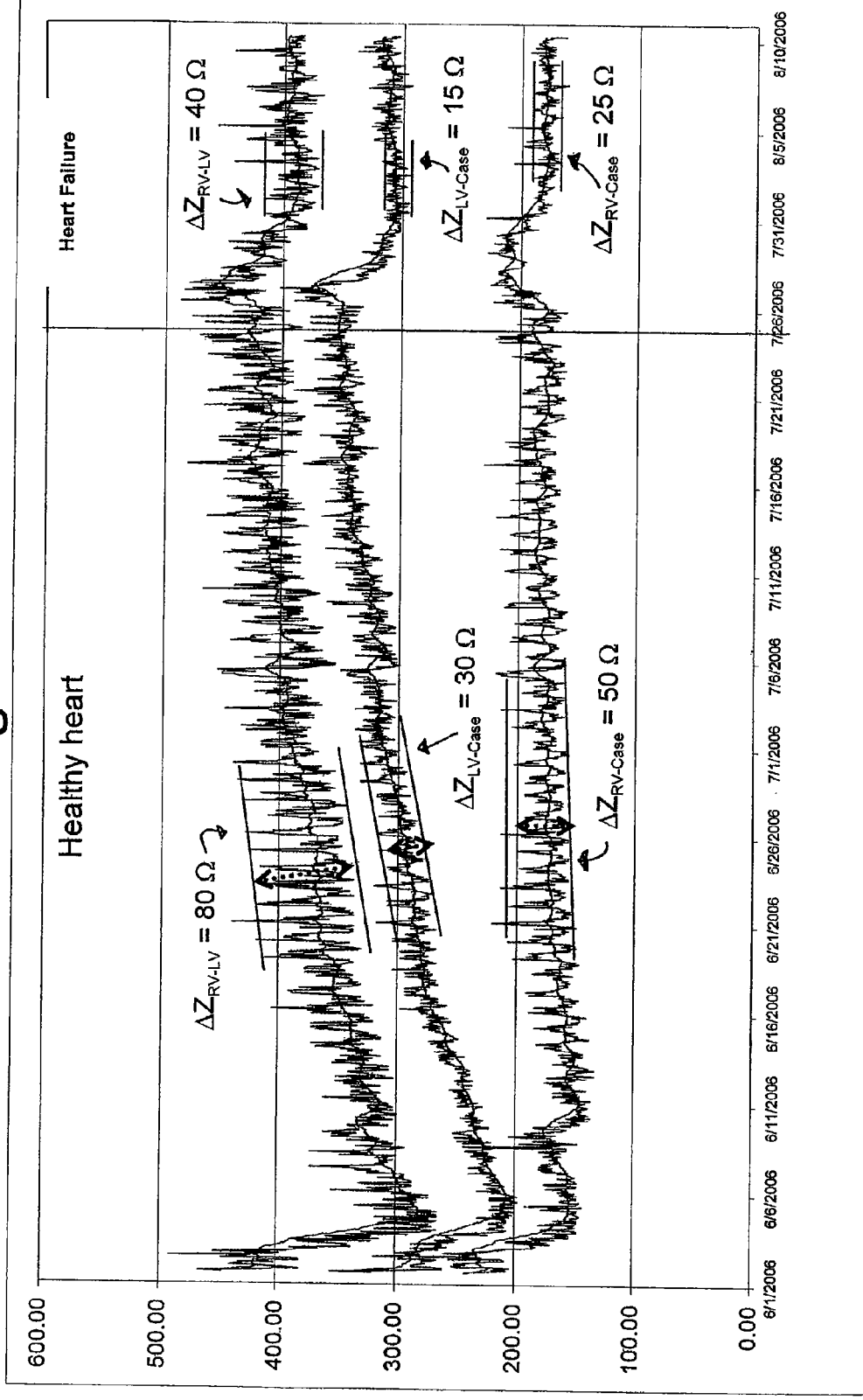
FIG. 8 illustrates an impedance trend showing three different impedance curves a heart that is at first healthy and then suffers from heart failure.

FIG. 8 illustrates one embodiment of an impedance trend 800, where the impedance $Z_{a-b}$ or electrical resistance, between two points (a and b) in the body is shown over time. For example, the impedance can be measured between various electrode pairs, such as the left ventricular (LV) ring and right ventricular (RV) ring electrode pair, the LV ring and case electrode pair, the RV ring and case pair, or the RV coil and case pair, etc. The curves 802, 804, 806, and 807 show the oscillations in internal impedance over about a two month period measured at four pairs of locations within the body.

Curve 802 shows the impedance between a patient's right and left ventricles over time. The impedance is measured between the LV ring and RV ring electrodes. Curve 804 shows the impedance between a patient's left ventricle and the case or housing of an implantable device, such as any of the implantable devices discussed above. The impedance is measured between the LV ring and case electrodes. Curve 806 shows the impedance between a patient's right ventricle and the case or housing of an implantable device, such as any of the implantable devices discussed above. The impedance is measured between the RV ring and case electrodes. Curve 807 shows the impedance between a patient's right ventricle at the pacing coil and the case. The impedance is measured between the RV coil and case electrodes.

A circadian impedance difference 808, 810, 812 can be determined by subtracting the maximum impedance from the minimum impedance for each day. In addition, a daily mean impedance value can be determined as well.

The impedance values, circadian differences and average values can be processed similarly to any of the methods discussed above. For example, instead of determining the onset of an adverse cardiac condition based upon changes in a patient's LAP, such determinations can be made based upon changes in the patient's cardiac impedance.

For example, curves 802, 804, and 806 show that the impedance difference of a healthy patient is 80Ω, 30Ω, and 50Ω, respectively. However, when the same patient begins to experience heart failure, the circadian impedance difference drops by approximately 50% to 40Ω, 15Ω, and 25Ω, respectively.

As described herein, one or more hemodynamic parameters, such as LAP and cardiac impedance, are used to detect, diagnose, or predict an adverse cardiac condition. Other hemodynamic parameters include stroke volume and cardiac output. Stroke volume is the volume of blood ejected from a ventricle of the heart with each beat of the heart. Cardiac output is the volume of blood being pumped by the heart in a minute. Cardiac output is typically defined as the product of a patient's stroke volume and heart rate. For example, the following data was recorded from a healthy heart, a heart in heart failure, and a heart in severe heart failure. Left ventricular volume, stroke volume, ejection fraction, left atrial volume, dyssynchrony index, mitral regurgitation (MR) scale and left ventricular end diastolic pressure (LVEDP) were determined and recorded as follows. It can be seen that these physiological parameters correlated to changes in left atrial pressure, as predicted by the LVEDP, and can therefore be used alternatively or in conjunction with left atrial pressure measurements to determine or predict adverse cardiac conditions, as discussed herein.

| Condition | LV Vol. [ml] | Stroke Vol. [ml] | Eject. Fr. [%] | LA Vol. [ml] | Dys. Ind. [ms] | MR Scale | LVEDP [mmHg] |
| --- | --- | --- | --- | --- | --- | --- | --- |
| Healthy Heart | 82 | 36 | 43.9 | 23 | 30.6 | 0.5 | 3 |
| Heart Failure | 104 | 30 | 28.8 | 21 | 29.1 | 1 | 12 |
| Severe Heart Failure | 119 | 15 | 12.6 | 39 | 53.8 | 2 | 28 |

When measuring trends or variations in hemodynamic parameter data, an adverse cardiac condition can be detected when a certain value (such as a mean or a delta) deviates significantly from historical known data from the same patient. Alternatively, an adverse cardiac condition can be detected when a certain value (such as a mean or a delta) deviates significantly from know values of health, which are accumulated from one or more subjects other than the patient. For example, data may be compared against the patient's own past data, or may be compared against a cohort of data, which may or may not include the patient's data.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed is:

1. A method of determining the status of an adverse cardiac condition of a medical patient, the method comprising:
   determining a series of first values of a hemodynamic parameter during a first time period from a sensor implanted within the medical patient, wherein the first time period is during the daytime;
   determining a series of second values of the hemodynamic parameter during a second time period from the sensor, wherein the second time period is during the nighttime;
   calculating, with a signal processor, a first average value of the series of first values and a second average value of the series of second values;
   calculating a difference between the first average value and the second average value; and
   providing an indication of an adverse cardiac condition when the difference is less than a first predetermined threshold value;
   wherein the hemodynamic parameter comprises a left atrial pressure of the patient's heart.

2. The method of claim 1, wherein the first and second periods correspond to non-overlapping portions of a circadian rhythm.

3. The method of claim 1, wherein the adverse cardiac condition comprises a heart failure exacerbation.

4. The method of claim 1, wherein the adverse cardiac condition comprises an acute cardiac event.

5. The method of claim 1, wherein the adverse cardiac condition is heart failure.

6. The method of claim 1, wherein the adverse cardiac condition is pulmonary edema.

7. The method of claim 1, wherein the first predetermined threshold value is in a range of about 30-50% of a historical variation of the patient.

8. The method of claim 1, wherein the first predetermined threshold value is in a range of about 50-70% of a historical variation of the patient.

9. The method of claim 1, further comprising calculating a mean value of the first average value and the second average value; and providing an indication of an adverse cardiac condition when the difference is less than a first predetermined threshold value and the mean value is greater than a second predetermined threshold.

10. An apparatus for treating cardiovascular disease in a medical patient, the apparatus comprising:
    a housing configured to be implanted within a medical patient;
    an implantable sensor, operable to generate a sensor signal indicative of a hemodynamic parameter of the medical patient;
    at least one implantable lead having a proximal end and a distal end, the implantable lead coupled to the implantable housing at the proximal end and further coupled to the sensor;
    a signal processor located within the housing, the signal processor operable to monitor circadian variations in the hemodynamic parameter of a medical patient by comparing a first data set taken during the daytime with a second set taken during the nighttime and determine an occurrence of an adverse cardiac condition based upon a change in the circadian variations over a predetermined time period;
    wherein the hemodynamic parameter comprises a left atrial pressure of the patient's heart.

11. The apparatus of claim 10, wherein the sensor is intended to be positioned within the heart.

12. The apparatus of claim 10, wherein the implantable sensor comprises a pressure transducer.

* * * * *